(12) United States Patent
Scheiner et al.

(10) Patent No.: US 11,623,086 B2
(45) Date of Patent: Apr. 11, 2023

(54) SYSTEM AND METHOD FOR THERAPY

(71) Applicant: Medtronic Xomed, Inc., Jacksonville, FL (US)

(72) Inventors: Avram Scheiner, Vadnais Heights, MN (US); James Britton Hissong, Jacksonville, FL (US); Rebecca J. Haag, Broomfield, CO (US); Randal C. Schulhauser, Phoenix, AZ (US)

(73) Assignee: MEDTRONIC XOMED, INC., Jacksonville, FL (US)

( * ) Notice: Subject to any disclaimer, the term of this patent is extended or adjusted under 35 U.S.C. 154(b) by 275 days.

(21) Appl. No.: 16/752,236

(22) Filed: Jan. 24, 2020

(65) Prior Publication Data

US 2021/0228871 A1    Jul. 29, 2021

(51) Int. Cl.

| A61N 1/36 | (2006.01) |
| G16H 20/30 | (2018.01) |
| G16H 50/70 | (2018.01) |
| G16H 50/20 | (2018.01) |
| A61N 1/372 | (2006.01) |
| A61N 1/378 | (2006.01) |

(52) U.S. Cl.
CPC ....... *A61N 1/36003* (2013.01); *A61N 1/3787* (2013.01); *A61N 1/37217* (2013.01); *G16H 20/30* (2018.01); *G16H 50/20* (2018.01); *G16H 50/70* (2018.01)

(58) Field of Classification Search
CPC ..... A61N 1/36003; G16H 20/30; G16H 50/70
USPC .......................................................... 607/42
See application file for complete search history.

(56) References Cited

U.S. PATENT DOCUMENTS

| 4,395,731 A | 7/1983 | Schoolman |
| 6,901,941 B2 | 6/2005 | Gershtein et al. |
| 7,001,045 B2 | 2/2006 | Gregerson et al. |
| 7,106,825 B2 | 9/2006 | Gregerson et al. |
| 7,108,421 B2 | 9/2006 | Gregerson et al. |
| 7,188,998 B2 | 3/2007 | Gregerson et al. |
| 8,238,631 B2 | 8/2012 | Hartmann et al. |
| 8,467,133 B2 | 6/2013 | Miller |
| 8,600,478 B2 | 12/2013 | Verard et al. |
| 8,644,907 B2 | 2/2014 | Hartmann et al. |
| 8,670,816 B2 | 3/2014 | Green et al. |
| 8,842,893 B2 | 9/2014 | Teichman et al. |
| 8,891,847 B2 | 11/2014 | Helm et al. |
| 9,339,651 B2 | 5/2016 | Meadows et al. |
| 9,411,057 B2 | 8/2016 | Helm et al. |

(Continued)

FOREIGN PATENT DOCUMENTS

| EP | 2389224 A2 | 11/2011 |
| EP | 3071288 B1 | 11/2018 |

(Continued)

OTHER PUBLICATIONS

International Preliminary Report on Patentability dated Apr. 4, 2019 in corresponding/related International Application No. PCT/US2017/052411.

(Continued)

*Primary Examiner* — Nadia A Mahmood
(74) *Attorney, Agent, or Firm* — Shumaker & Sieffert, P.A.

(57) ABSTRACT

Disclosed is a system for stimulation of a subject. The stimulation may be to provide therapy to treat the subject. Stimulation may be of selected muscle groups and/or portions.

22 Claims, 12 Drawing Sheets

(56) References Cited

U.S. PATENT DOCUMENTS

| | | |
|---|---|---|
| 9,412,200 B2 | 8/2016 | Helm et al. |
| 9,486,628 B2 | 11/2016 | Christopherson et al. |
| 9,675,319 B1 | 6/2017 | Razzaque et al. |
| 9,757,560 B2 | 9/2017 | Papay |
| 9,807,860 B2 | 10/2017 | Helm et al. |
| 9,889,299 B2 | 2/2018 | Ni et al. |
| 10,029,098 B2 | 7/2018 | Papay |
| 10,065,038 B2 | 9/2018 | Papay |
| 10,744,339 B2 | 8/2020 | Makansi |
| 2005/0203367 A1 | 9/2005 | Ahmed et al. |
| 2005/0289472 A1 | 12/2005 | Morita et al. |
| 2009/0088634 A1 | 4/2009 | Zhao et al. |
| 2009/0088830 A1 | 4/2009 | Mohamed et al. |
| 2010/0290690 A1 | 11/2010 | Hartmann et al. |
| 2012/0099772 A1 | 4/2012 | Helm et al. |
| 2012/0197338 A1 | 8/2012 | Su et al. |
| 2012/0250822 A1 | 10/2012 | Helm et al. |
| 2013/0060146 A1 | 3/2013 | Yang et al. |
| 2013/0188848 A1 | 7/2013 | Helm et al. |
| 2013/0237811 A1 | 9/2013 | Mihailescu et al. |
| 2014/0135868 A1 | 5/2014 | Bashyam |
| 2014/0200622 A1 | 7/2014 | Terry, Jr. et al. |
| 2014/0275989 A1 | 9/2014 | Jacobsen et al. |
| 2015/0142120 A1 | 5/2015 | Papay |
| 2015/0190630 A1 | 7/2015 | Kent et al. |
| 2015/0224307 A1* | 8/2015 | Bolea .................. A61N 1/3601 607/42 |
| 2015/0363979 A1 | 12/2015 | Takano et al. |
| 2016/0030131 A1 | 2/2016 | Yang et al. |
| 2016/0191887 A1 | 6/2016 | Casas |
| 2016/0220324 A1 | 8/2016 | Tesar |
| 2016/0242623 A1 | 8/2016 | Pasini et al. |
| 2016/0324580 A1 | 11/2016 | Esterberg |
| 2017/0087360 A1 | 3/2017 | Scheiner |
| 2017/0151432 A1 | 6/2017 | Christopherson et al. |
| 2017/0202633 A1 | 7/2017 | Liu |
| 2018/0015282 A1 | 1/2018 | Waner et al. |
| 2018/0042681 A1 | 2/2018 | Jagga |
| 2018/0078316 A1 | 3/2018 | Schaewe et al. |
| 2018/0221660 A1 | 8/2018 | Suri et al. |
| 2020/0016401 A1 | 1/2020 | Papay et al. |
| 2020/0155840 A1 | 5/2020 | Giannoukos et al. |
| 2020/0269044 A1 | 8/2020 | Papay |
| 2020/0282215 A1 | 9/2020 | Scheiner et al. |
| 2020/0338358 A1 | 10/2020 | Makansi |
| 2020/0346017 A1 | 11/2020 | Caparso et al. |

FOREIGN PATENT DOCUMENTS

| | | |
|---|---|---|
| WO | 92/15364 A1 | 9/1992 |
| WO | 2012075155 A2 | 6/2012 |
| WO | 2015/123360 A1 | 8/2015 |
| WO | 2017112960 A1 | 6/2017 |
| WO | 2020/181124 A2 | 9/2020 |

OTHER PUBLICATIONS

International Preliminary Report on Patentability dated Jun. 18, 2020 in corresponding/related International Application No. PCT/US2018/064280.

International Search Report and Written Opinion dated Feb. 22, 2019 in corresponding/related International Application No. PCT/US2018/064280.

International Search Report and Written Opinion dated Jan. 2, 2018 in corresponding International Application No. PCT/US2017/052411.

International Search Report and Written Opinion regarding International Application No. PCT/US2021/013877, dated May 6, 2021.

International Search Report and Written Opinion regarding International Application No. PCT/US2021/013882, dated Apr. 19, 2021.

International Search Report and Written Opinion regarding International Application No. PCT/US2021/013889, dated Apr. 21, 2021.

International Search Report and Written Opinion regarding International Application No. PCT/US2021/013892, dated May 19, 2021.

Invitation to Pay Additional Fees dated Nov. 20, 2017 in corresponding International Application No. PCT/US2017/052411.

Mathies "Augmented reality comes to neurosurgery with tech developed by Leica" 2 pages, Aug. 6, 2016. http://www.digitaltrends.com/cool-tech/leica-captview-ar-brain-surther/#ixzz4KAChTpm8.

NewTom Cone Beam 3d Imaging product brochure, 12 pages, 2017.

ODG Smartglasses 9 product brochure, 2 pages, 2018.

Straka "A.R. Enhanced Navigated Biopsy Storyboard" Medtronic Neurosurgery, Feb. 2016, 11 pages.

International Preliminary Report on Patentability from International Application No. PCT/US2021/013877 dated Aug. 4, 2022, 9 pp.

* cited by examiner

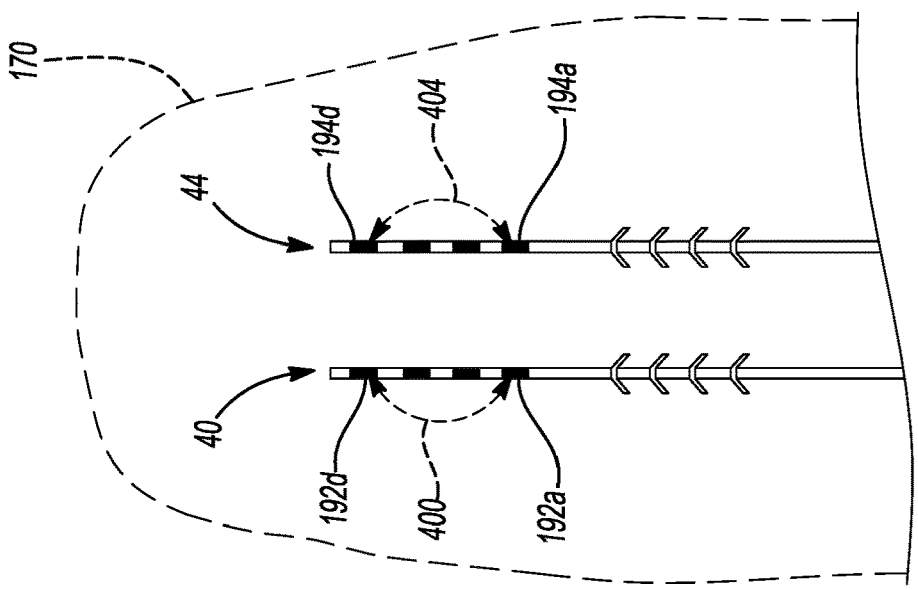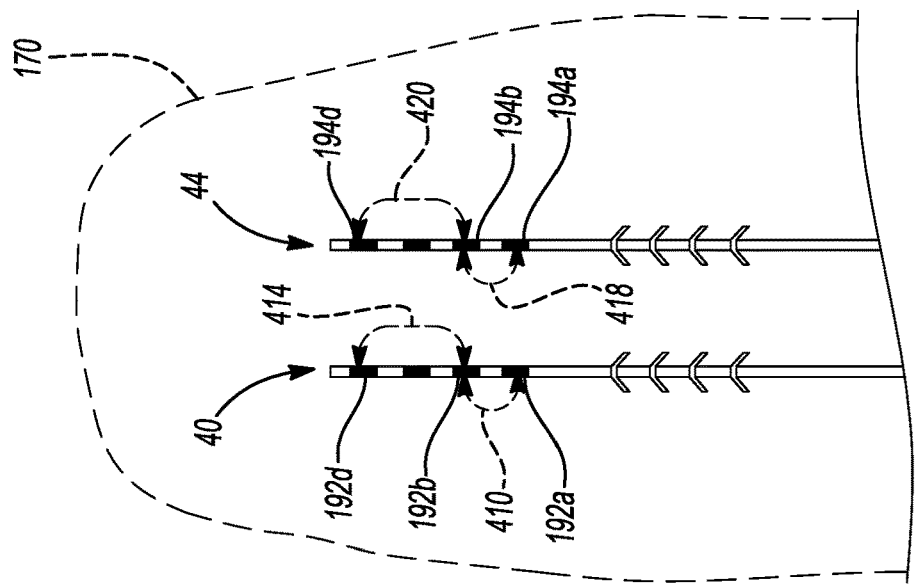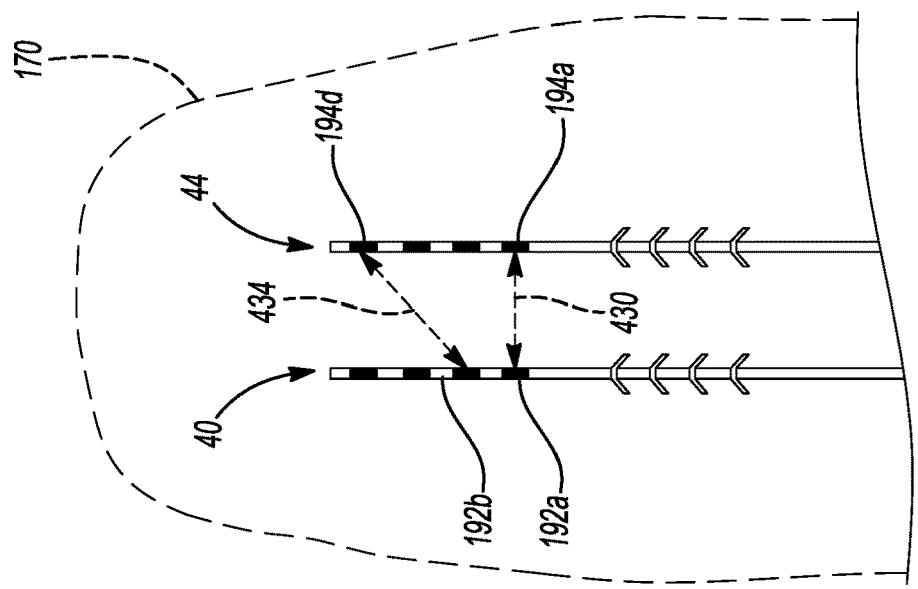
Fig-6A
Fig-6B
Fig-6C

SYSTEM AND METHOD FOR THERAPY

CROSS-REFERENCE TO RELATED APPLICATIONS

This application includes subject matter related to U.S. patent application Ser. No. 16/752,253, filed on Jan. 24, 2020; U.S. patent application Ser. No. 16/752,274, filed on Jan. 24, 2020; and U.S. patent application Ser. No. 16/752,285, filed on Jan. 24, 2020. The entire disclosure(s) of (each of) the above applications are incorporated herein by reference.

FIELD

Disclosed is a system to apply therapy to a subject, and particularly to provide therapy regarding stimulation and/or activation of muscle tissue.

BACKGROUND

This section provides background information related to the present disclosure which is not necessarily prior art.

A subject may have a condition that may be harmful to the subject, such as over a period of time. One condition may include obstruction of an airway for an air-breathing subject, such as a human. Several conditions exist that may obstruct an airway and are generally referred to as obstructive sleep apnea (OSA) and/or upper airway restrictive/resistance syndrome (UARS).

OSA and UARS may affect a subject by limiting airflow and, therefore, oxygen saturation. Low oxygen saturation may lead to various further undesired conditions. Treatment of these conditions often requires an external device to assist in providing airflow to a subject.

SUMMARY

This section provides a general summary of the disclosure, and is not a comprehensive disclosure of its full scope or all of its features.

Treatment of obstructive sleep apnea (OSA) and/or upper airway restrictive/resistance syndrome (UARS) may be provided by stimulating a selected portion of a subject. The stimulation may be provided by an implanted device. Thus, the treatment may be provided without an externally worn or applied system. Treatment, therefore, may be automatic and less or non-obtrusive.

In various embodiments, a stimulation system may be provided to a subject to stimulate various portions of the subject. The stimulation system may include a system that is able to provide an electrical stimulation, or other appropriate stimulation, from a source to a subject, such as through a lead. The lead may include one or more contacts or electrodes to provide the stimulation from the source to the selected area. The source may include a generator and/or a power source to provide the stimulation to a selected area.

To treat OSA and/or UARS the stimulation may be to a portion of a lingual muscle. The stimulation may be provided through the lead from an implanted stimulator according to at least one waveform and/or configuration. Further, the system may include a learning and/or testing phase to select one or more patterns or configurations. The selected patterns may be predetermined or determined in real time based on feedback from selected one or more sensors and/or individuals (e.g. subject, clinician, etc.)

In various embodiments, the subject may be a mechanical system to which a stimulation, such as an electrical stimulation, may be provided. For example, a powered component may be provided with an electrical stimulation to provide movement of a selected portion of the powered components. In various embodiments, however, the stimulation may be provided to a human subject or an animal subject to stimulate a selected portion of the subject. The stimulation may include the electrical stimulation to cause a selected muscle to activate and stiffen or contract. Contraction of a muscle, as is generally understood by one skilled in the art, may cause a muscle to contract and shorten to cause movement of a selected subject portion, such as an appendage, a muscle tissue portion, or other selected portion of the subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIGS. 6A to 6C illustrate exemplary lead contact stimulation configurations (e.g. bipolar from an anode to a cathode) for stimulation of a subject, according to various embodiments;

Corresponding reference numerals indicate corresponding parts throughout the several views of the drawings.

DETAILED DESCRIPTION

Example embodiments will now be described more fully with reference to the accompanying drawings.

Figure 1:
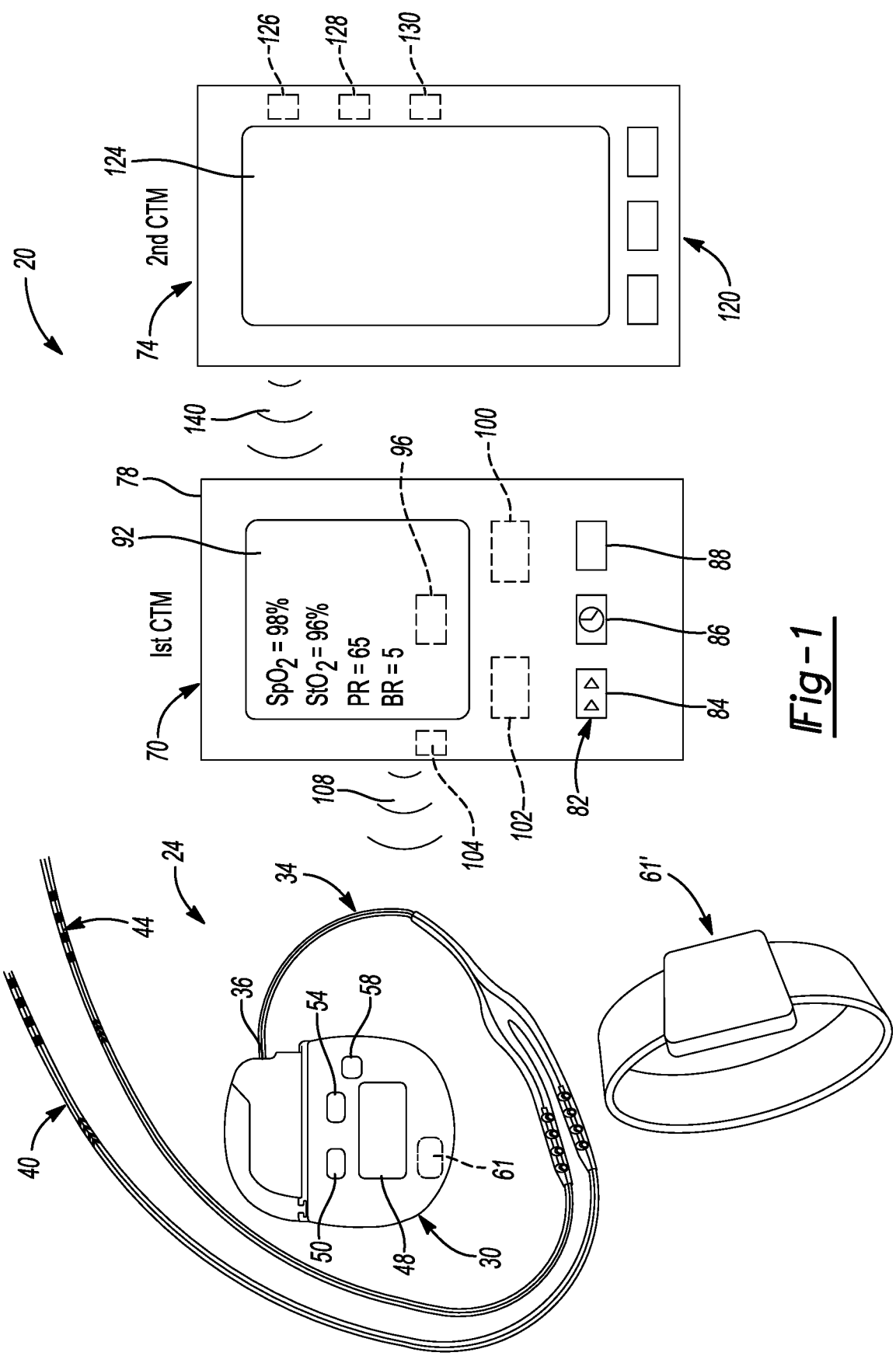
FIG. 1 is a schematic illustration of a stimulation system.
Figure 2:
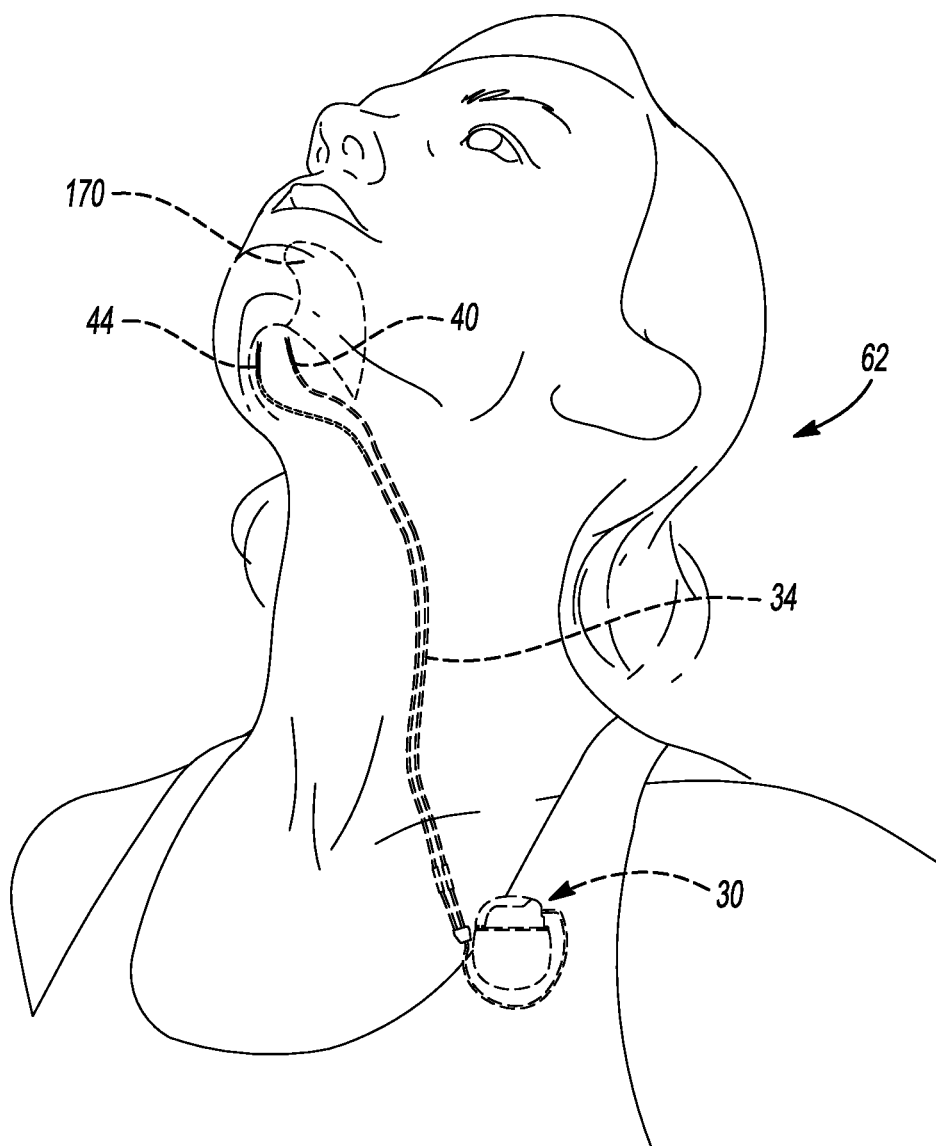
FIG. 2 is a schematic illustration of an implantation position of a stimulation system.

With initial reference to FIG. 1 and FIG. 2, a stimulation assembly or system 20 is illustrated. The stimulation system 20 may include various components, or selected components of the system 20 as discussed further herein. In various embodiments, the stimulation system 20 may be provided for treatment of Obstructive Sleep Apnea (OSA) and/or upper airway restrictive/resistance syndrome (UARS). The stimulation system 20 may include various features and/or systems for the treatment, such as an implantable stimulation assembly 24 that may include, according to various embodiments, an implantable device (ID) 30. The ID may be implanted and operated (e.g. by instructions stored therein) to provide stimulation to a lingual muscle (i.e. tongue) of a subject 62. The stimulation may be provided to ensure maintaining an open airway and/or re-open an airway.

The ID 30 may be implanted in the subject 62, as discussed herein. Interconnected with the ID 30, as a part of the implantable stimulation assembly 24, may be one or more lead assemblies 34. In various embodiments, for example, the lead assembly 34 may be connected to the ID 30 at a selected connection point 36 and extend to a first lead or stimulator portion (also referred to as a lead end) 40, and a second lead or stimulator portion (also referred to as a lead end) 44. In various embodiments, as also discussed further herein, stimulation may be provided to the subject through the lead ends 40, 44 to treat the OSA and/or UARS condition of the subject 62. The two lead ends 40, 44 may be used in selected or varying manners to reduce or eliminated fatigue of the lingual muscle to assist in increasing efficacy or success of a treatment.

The ID 30 may also include various components such as a power source (e.g. a battery) 48. The battery 48 may be rechargeable and recharged in a selected manner, such as through inductive recharging, which is generally understood in the art. The battery 48 may be charged via a wired or wireless charging system. Wireless or contactless recharging modalities may include inductive recharging, resonant recharging, etc. Exemplary stimulation systems that include rechargeable batteries include the Intellis® implantable neuro stimulator sold by Medtronic, Inc. having a place of business in Minneapolis, Minn. It is understood, however, that any appropriate power storage system may be provided and the battery is merely exemplary. The power source 48 is to provide a selected current and/or voltage between one or more electrodes of the lead assembly 34, as discussed further herein.

The ID 30 may further include selected components to assist in providing stimulation through the lead assembly 34. For example, the ID 30 may include a processor module 50 that may be any appropriate processor, as discussed further herein, to execute instructions provided to the ID 30 from an external source and/or saved on a memory module 54. The memory module 54 may be any appropriate memory system, such as those discussed further herein. Further, the ID 30 may include a selected transceiver system or module 58 that may be used to transmit and/or receive information and/or instructions from an external source. The transceiver module 58 may be any appropriate transceiver module such as those discussed further in.

The stimulation assembly 20 may include, according to various embodiments, the implantable stimulation portion 24 as a stand-alone system. In various embodiments, the memory module 54 may include any appropriate instruction and/or algorithms for operation of the stimulation portion 24. The processor module 50 may execute the instructions from the memory module 54 and the battery 48 may be provided to power the stimulation portion 24. It is understood, however, that various portions may also be provided external to a subject 62 (FIG. 2) to assist in interacting with the ID 30.

Various sensors may be provided to transmit and/or receive a signal regarding the subject 62. A sensor 61 may be included with the ID 30 (e.g. formed on an exterior of the ID 30, placed within the ID 30, and/or connected to the ID 30). The sensor 61 may include one or more of an accelerometer, a global positioning system, oximeter, electromyography sensor, etc. The sensor 61 may be used to assist in determining selection of treatment for the subject 62, as discussed herein. It is understood that the sensor 61 may also communicate with other systems. Also, or in addition to the sensor 61, an external or wearable sensor 61' may be placed on the subject 62. The wearable sensor 61' may be the same sensors as discussed above, including redundant thereto. The wearable sensor 61' may also include additional or different sensors. Sensors, particularly external sensors, may include a position (e.g. relative to gravity) sensor, temperature sensor, $CO_2$ detector, airflow (e.g. nasal or mouth) detector, microphone (e.g. for detecting breathing sounds (like snoring), impedance detector (e.g. to detect lung volume). Further, various sensors may be used to determine or monitor "quality of sleep" such as sensing via EEG or integration of various sensors already mentioned. A quality of sleep determination may be correlated to OSA therapy effectiveness. Regardless of the type, the sensor in the wearable sensor 61' may also communicate with the ID 30 and/or other portions of the system 20.

External systems, as a part of the stimulation assembly 20, may include a first external controller or transceiver 70. The first external transceiver 70 may also be referred to as a communication telemetry module (CTM) 70 that may communicate with the ID 30. In various embodiments, the stimulation assembly 20 may further include a second transmission and/or control module (CTM) 74. The second control module 74 may communicate with the first control module 70, for various purposes as discussed further herein, may communicate directly with the ID 30, and/or may communicate with the ID 30 through the first transmission module 70. It is understood, however, that only one of the first transmission modules 70 or the second transmission module 74 may be provided for the stimulation assembly 20.

The first CTM 70 may be provided to the user 62 for a personal and/or at home use. As discussed further herein, the CTM 70 may be used by the user 62 to assist in controlling the ID 30 to provide stimulation to the user 62. The CTM 70 may also be used to alter operation of the ID 30, such as by the user 62, input indications from a user 62, or other appropriate mechanisms.

Briefly, the CTM 70 may include a body or module portion 78 that is sized to fit within a hand of the user 62. Accordingly, the CTM 70 may be mobile relative to the user 62 and/or allow for ease of transport and use by the user 62. Further, the CTM 70 may be positioned near the user 62 at any appropriate time, such as during a selected or near a sleep period of the user 62. The CTM 70 may further include one or more input portions, such as a physical or also referred to as a hard button or hard selection assembly 82 that may include one or more buttons that allow the user 62 to input operation or select operations of the ID 30. For example, the hard buttons 82 may include a start and stop button 84, a timer button 86, and/or a power or emergency button 88. The CTM 70 may also include a selected display 92 to provide information to the user 62 such as a pulse rate, oxygen saturation value, breathing rate, or other appropriate information. The display 92 may provide information, such as historical information, to a clinician for selecting programming and operation of the ID 30. The display 92 may also be a touchscreen or touch sensitive and, therefore, include one or more soft buttons.

The CTM 70 may include various components, such as a processor module 100, a memory module 102, and a communication or transceiver module 104. The processor module 100, the memory module 102, and the transceiver module 104 may be similar to those discussed further herein. As illustrated in FIG. 1, the CTM 70 may transmit a signal, such as a wireless signal 108 to the ID 30. Further, the ID 30 may transmit a signal, such as a wireless signal 110, to the CTM 70. Accordingly, the CTM 70 may receive information from the ID 30 and/or transmit information to the ID 30, and vice versa. As discussed herein, the CTM 70 may be used to program or select operation of the ID 30 and the ID 30 may include sensors to transmit information to the CTM 70. The CTM 70 may be configured as any appropriate device and/or may be incorporated as an application with an appropriate mobile computer (e.g. mobile phone, tablet, etc.). The application may be made for any appropriate operating system such as the iOS operating system, Android® operating system, etc. Also, the CTM 70 may be powered in an appropriate manner, such as with an internal battery that may be charged via a wired or wireless charging system. Wireless or contactless recharging modalities may include inductive recharging, resonant recharging, etc.

The stimulation assembly 20 may further include a second control module, such as a CTM 74. The CTM 74 may include components similar to the first CTM 70. The CTM 74, however, may be a larger and/or permanent device provided with a clinician for operation of the ID 30 and/or programming of the first CTM 70. The second CTM 74 may generally be non-mobile, in other words not intended to be moved with or by the subject 62. Accordingly, the second CTM 74 may include various hard buttons 120, a touch screen 124, a processor module 126, a memory module 128, and a transceiver module 130. Thus, the CTM 74 may transmit a signal, such as a wireless signal 140, to the first CTM 70 and/or the ID 30. Thus, the ID 30 may also transmit the signal 110 to the CTM 74 and/or the first CTM 70 may transmit a signal to the second CTM 74.

Accordingly, the simulation assembly 20 may include various components for operation of the ID 30 according to selected embodiments, and in various applications. The ID 30 may be implanted in the subject 62 for stimulation of the subject 62 according to a selected mechanism or method, as discussed further herein. Various control modules may be provided at selected times to allow for programming of the ID 30, altering of the programming of the ID 30, receiving output (e.g. historical sensor data) from the ID 30, and analysis of operation of the ID 30, historical data, and other information. In this manner, the first CTM 70 may be provided for substantially immediate use and/or adjacent use during operation and/or after implantation of the ID 30. The second CTM 74 may be provided for initial programming, follow up, and interaction with the subject and/or a central data storage and/or analysis system by selected users, such as the clinician.

With continuing reference to FIG. 1 and additional reference to FIG. 2, the stimulation portion 24 may be implanted into a selected subject 62. As illustrated in FIG. 2, the selected subject 62 may be a human subject. It is understood, however, that any appropriate subject may have the stimulation portion 24 positioned therewith at appropriate times. It is further understood that the ID 30 may be positioned near or external to the subject 62 such that the lead portion 34 is implanted percutaneously into the subject 62 and the stimulation portion 30 (e.g. power and control) is exterior to the subject. Therefore, the discussion herein of an implantable device 30 will not be understood to eliminate selected components, such as a power source, stimulation reconnection, or other features or portions that may be placed in an external device for percutaneous transmission through the lead assembly 34 to a stimulation location of the subject 62.

With continuing reference to FIG. 2, the ID 30 may be implanted in the subject 32 in any appropriate location, such as in an abdominal wall, a chest wall, sub-dermally near a clavicle, or other appropriate locations. The lead assembly 34 may be connected to the ID 30 and pass through selected tissue to a selected location for stimulation of the subject 62. In various embodiments, as illustrated in FIG. 2, the stimulation lead assembly 34, including the first and second lead tip portions 40, 44 may be positioned in a lingual tissue (i.e. a tongue 170). The lead assembly 34 may be positioned in the subject 62 along a single path for a selected portion of the length of the lead assembly 34 and/or may be immediately divided into two lead portions for positioning in the tongue 170. As one skilled in the art will understand, the tongue may be formed of a plurality of muscle portions that may act in concert to cause movement of the tongue 170. Accordingly, reference to the tongue 170 is understood to refer to relevant portions of the tongue as discussed further herein. In addition, one skilled in the art will understand, the tongue 170 may include a plurality of nerve portions or constructs, including those discussed further herein, including nerve ends, endplates, etc.

Figure 3:
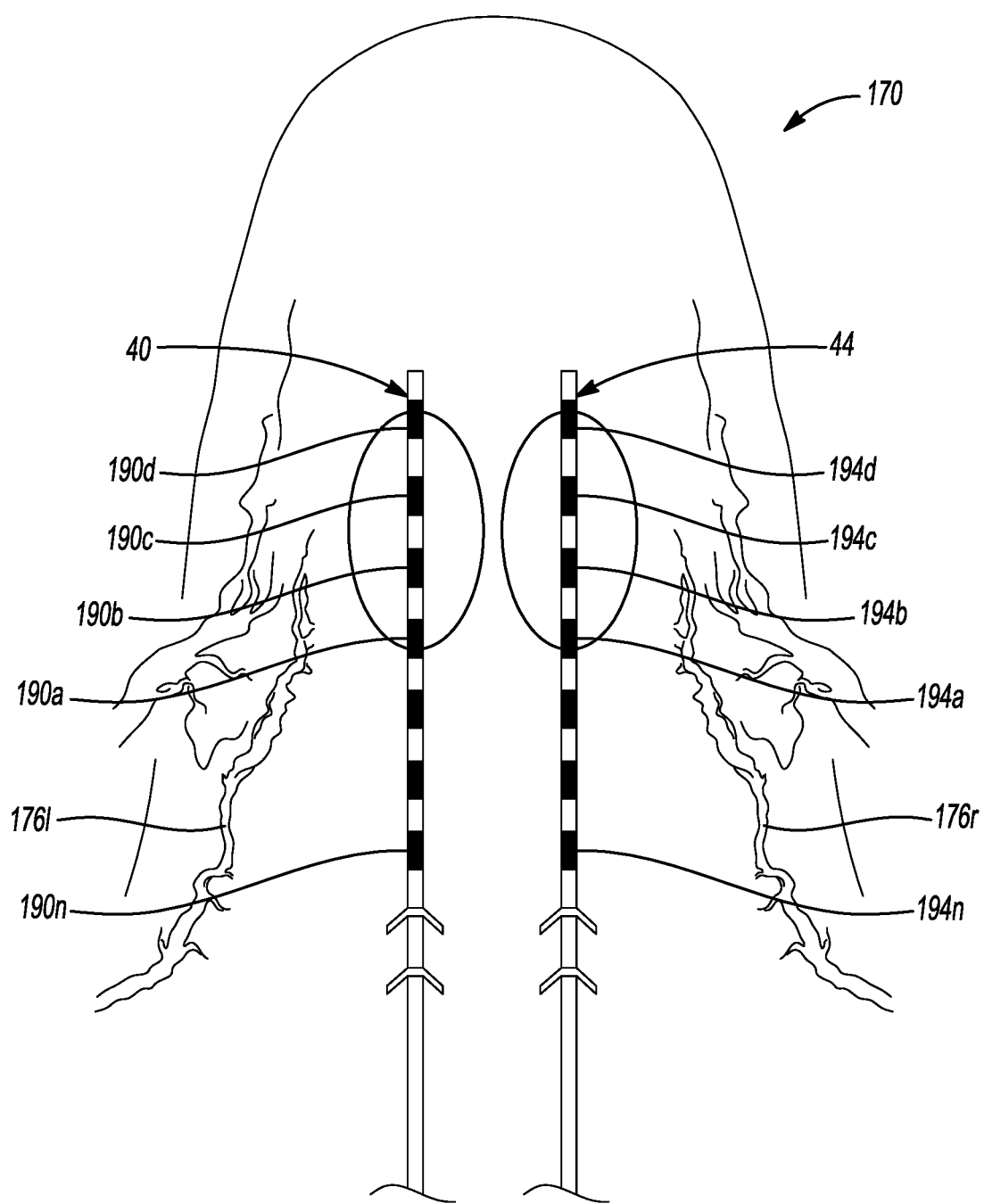
FIG. 3 is a detail superior-to-inferior view of a selected implantation location.
Figure 4:
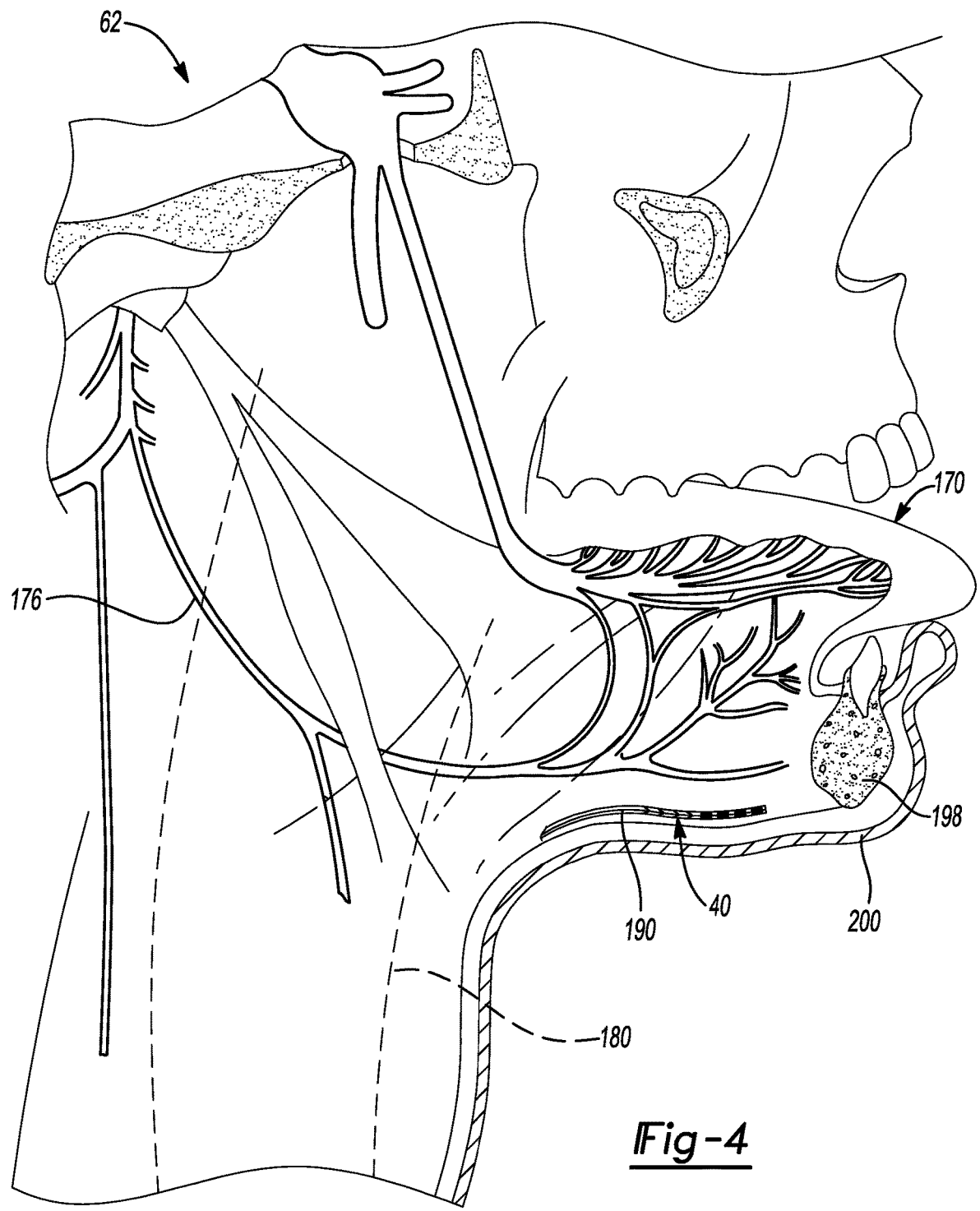
FIG. 4 is a medial-to-lateral view of a selected location of an implantation, according to various embodiments.

With continuing reference to FIG. 2 and additional reference to FIG. 3 and FIG. 4, the lead assembly 34 may be positioned at selected locations within the tongue 170. As illustrated in FIG. 2 and FIG. 3, the lead assembly 34 may include the first lead end or tip 40 and the second lead end or tip 44. Without being limited to the specific location of the two leads 40, 44, the first lead tip 40 may be a left lead tip and the second lead tip 44 may be a right lead tip. Further, it is understood, that the two lead tips 40, 44 may be substantially identical to one another save for a specific position relative to the tongue 170 (e.g. right and left). Therefore, discussion of one or a single lead tip, such as the lead tip 44, herein, is understood to be related to both lead tips unless specifically identified otherwise.

The tongue 170 may have branches of a hypoglossal nerve 176 therein. The hypoglossal nerve 176 may extend from the seventh cranial nerve and into the tongue 170. Natural, such as through signaling from the brain and spinal cord, innervation of the hypoglossal nerve 176 may cause movement or contraction of selected muscles in the tongue 170. The innervation of the hypoglossal nerve 176, therefore, may cause portions of the tongue 170 to contract and/or stiffen.

As is generally understood by one skilled in the art, an obstructive sleep apnea (OSA) may occur when all or part of the tongue 170 falls or collapses into the airway 180. Obstruction of the airway 180 may reduce or eliminate passage of air (e.g. including oxygen) to the subject 62. The obstruction may occur during a sleep cycle of the subject 62 and is therefore commonly referred to as OSA. A similar or related condition may be upper airway restrictive/resistance syndrome (UARS). Contraction of muscles in the tongue 170 may cause movement of the tongue 170 out of the airway 180 to reduce or treat OSA and/or UARS in the subject 62.

In some examples, an user (such as a surgeon) may implant the one or more leads 40, 44 such that one or more electrodes 190, 194 are implanted within soft tissue, such as musculature of the tongue 170, proximate to selected branches, such as medial branches, of one or both hypoglossal nerves 176. In some examples, one or more electrodes 190, 194 may be approximately 5 mm (e.g., about 2 mm to about 8 mm) from a major trunk of the hypoglossal nerve 176. In some examples, one or more electrodes 190, 194 may be placed in an area of protrusor muscles of the tongue 170 that include motor points, where each nerve axon terminates in the muscle (also called the neuro-muscular junction and/or nerve end plates). The motor points are not at one location but spread out in the protrusor muscles of the tongue 170. Leads 40, 44 may be implanted such that one or more electrodes 190, 194 may be generally in the area of the motor points (e.g., such that the motor points are within about 1 mm to about 10 mm from one or more electrodes 190, 194).

As described above, electrical stimulation therapy generated by IMD 30 and delivered via one or more electrodes 190, 194 may activate protrusor muscles to move tongue 170 forward, for instance, to promote a reduction in obstruction or narrowing of the upper airway 180 during sleep. As used herein, the term "activated" with regard to the electrical stimulation of protrusor muscles of the tongue 170 refers to electrical stimulation that causes depolarization or an action potential of the cells of the nerve (e.g., hypoglossal nerve(s)) innervating protrusor muscles of the tongue 170 and motor points and subsequent depolarization and mechanical contraction of the protrusor muscle cells of protrusor muscles of the tongue 170. In some examples, protrusor muscles of the tongue 170 may be activated directly by the electrical stimulation therapy.

In some examples, each one of electrodes 190, 194 may have equivalent electrode lengths (e.g., longitudinal extend of electrodes 190, 194 along lead body 40, 44). Lengths may be approximately 3 mm, but less than 3 mm lengths are possible. However, electrodes 190, 194 may have electrode lengths that are different from each other in order (e.g., to optimize placement of the electrodes 190, 194 or the resulting electrical field of stimulation relative to targeted stimulation sites corresponding to left and right hypoglossal nerves or branches of hypoglossal nerves and/or motor points of protrusor muscles of the tongue 170).

As illustrated in FIG. 3, the HG nerve 176 may include a left branch 176*l* and right branch 176*r*. The first or left lead tip or end 40 may be positioned on a left side of the tongue 170, which may be near the left branch 176*l*. The second or right lead tip or end 44 may be positioned on a right side of the tongue 170, which may be near the right branch 176*r*. Thus, the two lead ends 40, 44 may be provided bi-laterally or spaced apart laterally from one another. As illustrated in FIG. 3, the lead ends 40, 44 may be spaced apart from one another and away from a mid-lines of the tongue 170.

Providing the two lead tips 40, 44 to the tongue 170 may allow for selected stimulation pattern and/or bilateral stimulation within the tongue 170, as discussed further herein. Bilateral stimulation may include selected subject benefits, as discussed herein. The stimulation, therefore, may be bilateral. As discussed herein, the bilateral stimulation may be provided to ensure or limit muscle fatigue, selected tongue configuration, etc. Further, the bilateral stimulation may alternate left and right and/or may be simultaneous both left and right.

The lead 40 may be positioned within the tongue 170 in any appropriate manner, such as passing the lead 40 through a portion of the muscle of the tongue 170 and/or near nerve end plates. It is understood that the lead 40 and/or the lead tip 44 may be positioned near or adjacent selected nerves for stimulation of selected portions of the tongue 170. As illustrated in FIG. 3 and FIG. 4, the lead end 40 may include a plurality of electrodes or contact, such as four contacts 190, each referenced by a lowercase letter. Each of the electrodes or contacts 190 may be connected to the power source 48 and controlled individually and separately to provide stimulation to one or more portions of the tongue 170 It is understood that any appropriate number of contacts 190*n* may be provided. The stimulation through the electrodes 190 may be provided in any appropriate manner, such as discussed further herein. In various embodiments, for example, one of the electrodes, such as the electrode 190*a* may be operated as an anode while a second electrode, such as the contact 190*b*, may be operated as a cathode. Thus, a voltage differential may be generated between the two electrodes 190*a* and 190*b* to provide stimulation to one or more portions of the tongue 170. As discussed above, stimulation of the HG nerve 176 may cause contraction of one or more portions of the muscle of the tongue 170 and cause the tongue 170 to move out of the airway 180, at a selected time.

Briefly, the second lead tip 44 may also include one or more contacts, such as contacts 194, again each differentiated by a lowercase letter. It is understood that any appropriate number of contacts 194*n* may be provided. Again, each of the contacts 194 may be operated in a selected manner, such as selecting one to operate as an anode and another to operate as a cathode.

The lead tips 40, 44 may be operated in concert or together such that a lead electrode on the first lead tip 40, such as the electrode 190*a* may be operated as an anode and a second electrode, such as the electrode 194*a* on the second lead tip 44 is operated as a cathode. Thus, stimulation may be provided across the tongue 170 between the two lead tips 40, 44 (e.g. spaced apart on the tongue 170) and/or on a single side (e.g. along one side of the tongue 170) such as between the individual lead tips 40, 44. As also discussed further herein, the stimulation of the tongue 170 may be operated to be in a unilateral and/or bilateral manner. For example, the left side of the tongue may be stimulated with the first lead tip 40, followed by the right side of the tongue being stimulated by the second lead tip 44, followed by stimulation between the two lead tips 40, 44. It is also understood that various other possible stimulation anodes or techniques may also be provided, as also discussed further herein.

With continuing reference to FIGS. 3 and 4, the lead tips 40, 44 may be positioned in an appropriate portion of the tongue 170. Therefore, the lead tip 40 may be positioned substantially near an inferior portion of the tongue 170, such as near a bony portion of a mandible or lower jaw 198 and/or a fat or cutaneous layer 200 of the subject 62. Stimulation of one or more portions of the tongue 17076 has been discovered to cause contraction of selected muscle portions of the tongue 170 to cause the tongue tissue to move from or out of the airway 180 so as to open the airway 180 and remove an obstruction due to relaxation or movement of the tongue 170 into the airway 180.

In various embodiments, and without being limited to the theory, a selected position of the tongue may be that of an awake subject having an open airway for breathing without their tongue protruding from the mouth. Generally, to alleviate OSA with the stimulation therapy, the objective is to open or enlarge the upper airway. In various embodiments, this may stiffen the upper airway to prevent collapse during inspiration. This may occur through the stiffening of secondary muscles caused by stretching of those muscles when the primary muscle is stimulated and contracts. In addition, muscle contraction could occur by means of a centrally mediated reflex (i.e. a neural sensing signal is sent to the central nervous system which causes muscle contraction in the upper airway.

The stimulation system 20, including the stimulator portion or assembly 24, is provided to selectively stimulate portions of the subject 62, as discussed above. The stimulation of the subject 62 may be provided through the lead tips 40, 44 in a selected manner, such as bilaterally, unilaterally, switching unilaterally, and between the plurality of contacts 190, 194 of the respective lead tips 40, 44. With reference to FIGS. 5A through 5G, various types of stimulation may be provided to the tongue 170 via the lead assembly 34. The stimulation may be to one or more portions of the tongue 170 to cause activation of one or more selected muscle groups or portions. The activation of the muscle, such as due to the stimulation from the system 20, may cause contraction (including stiffening) of the muscle portions. Thus, stimulation of one or more selected one or more portions of the tongue 170 and/or nerve and/or nerve endplates may lead to activation of one or more muscle groups or portions.

The stimulation to one or more portions of the tongue 170 may be provided in a bilateral manner, such as to the left branch 176l and the right branch 176r. In a bilateral stimulation, the stimulation may be provided to both branches 176l, 176r simultaneously, alternating between the two branches, with a gap between the bilateral stimulation and/or with no gap. Further, the magnitude of stimulation in a bilateral manner may be the same or different and may vary over time. Various exemplary stimulation patterns are discussed and illustrated here. The bilateral stimulation may also cause bilateral (including simultaneous and/or bilateral alternating) activation of muscle groups in the tongue 170.

The various patterns, in various embodiments, may be provided for providing a non-continuous stimulation to at least selected portions, including the entirety, of the tongue 170. Nevertheless, even if non-continuous stimulation is provided to a particular portion or region of the tongue 170, a selected bilateral stimulation may allow for substantially continuous stimulation to at least selected portions of the tongue 170. Thus, the tongue 170 may be non-continuously stimulated, stimulated in a continuous manner bilaterally, or continuously stimulated in an alternating bilateral manner, or combinations thereof.

As illustrated herein, each of the lead ends 40, 44 may be operated for selected duty cycles. In various embodiments, the stimulation from either of t lead ends 40, 44 may be pulsed. The pulses may repeat, as discussed herein. The stimulation waveforms as illustrated in FIGS. 5A-5G may illustrated the duty system and have periods appropriate for providing therapy to the subject 62. Further, the stimulation may be provided at a selected magnitude form the ID 30. The magnitudes may refer to a selected frequency of provided during the on duty cycle (e.g. 10 Hz to about 200 Hz, including about 20 Hz to about 80 Hz), voltage (e.g. about 0.1 volts to about 15 volts, including about 0.1 volts to about 5 volts), amperage (e.g. about 0.1 milliamps to about 20 milliamps, including about 0.1 milliamps to about 15 milliamps). Ramp up and ramp down, as discussed herein, may include a gradual or selected increase or decrease of the above noted magnitudes.

Figure 5A:
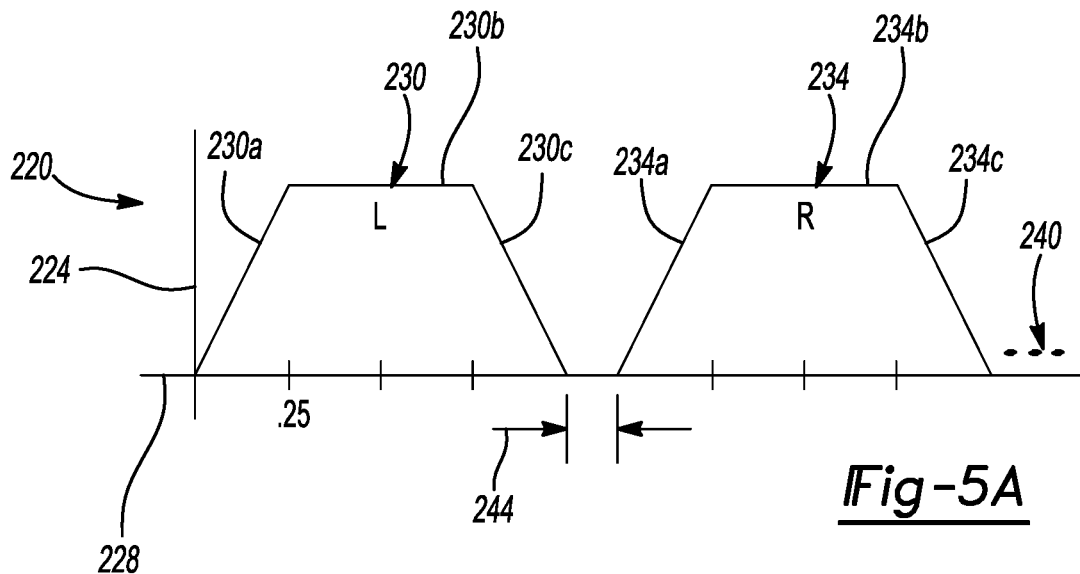
FIGS. 5A to 5G illustrate exemplary waveforms for stimulation of a subject, according to various embodiments.

With initial reference to FIG. 5A, stimulation may be provided as illustrated on the graph 220. The graph 220 illustrates two axes, including a magnitude y-axis 224 and a time x-axis 228. It is understood that the magnitude may be any appropriate magnitude including voltage, current, or the like. Further, the magnitude of stimulation may be based upon a selected subject and may be determined or learned from a specific subject and/or group of subjects (e.g. a group or population of subjects with similar characteristics). Accordingly, the graph of the stimulation is relative and may be provided for a specific subject based upon specific values therefor.

With continuing reference to FIG. 5A, the stimulation graph 220 may include a left stimulation portion 230 (i.e. provided with the left lead 40) and a right stimulation portion 234 (i.e. provided with the right lead 44). Each of the stimulation portions may each include respective ramp up phases 230a, 234a, a peak or selected stimulation 230b, 234b, and a ramp down phase 230c, 234c. The ramp up phases 230a, 234a and the ramp down phases 230c and 234c may be increasing or decreasing over time. In various embodiments, however, a ramp up or down may not be provided and the waves, therefore, may be substantially square. Accordingly, the ramp up and ramp down phase includes a varying magnitude over time and is merely exemplary. Ramp up and down, however, may be provided for subject comport, selected stimulation or contraction properties, etc.

The right and left stimulation portions 230, 234 may be initiated and then stopped to achieve a maximum stimulation 230b, 234b. Further the stimulation portions 230, 234 may be provided in a substantially repeating manner over a selected period of time, as discussed further herein. Accordingly, a repeating ellipsis symbol 240, may indicate that a repetition of the stimulation portions 230, 234 over a selected period or a selected time.

The stimulation portions including the left stimulation 230 and the right stimulation 234 may be separated by a selected time gap or time portion 244. Accordingly, the left stimulation portion 230 may stimulate or be caused to provide stimulation to only the left portion of the tongue 170 for a selected period of time, such as about 1 second. The stimulation of 1 second may be inclusive of the ramp up 230a and the ramp down 230c. Nevertheless, it is further understood that the stimulation of the left portion 230 may be any appropriate time and 1 second is exemplary for the current discussion. Similarly, the right stimulation portion 234 may be used to cause stimulation of only the right portion of the tongue 170 for a similar or substantially equal time, such as about 1 second. The left and right stimulations may be provided to only the left or right portion of the tongue 170 when the respective lead ends 40, 44 are operated to stimulate the one or more portions of the tongue 170.

As illustrated in the graph 220 the right stimulation portion and the left stimulation portion do not overlap and may be spaced apart from one another by a selected period of time, such as by the time gap 244. The time gap 244 may be an appropriate time, such as about 0.25 seconds. It is understood, however, that the time gap may be any appropriate time gap. In various embodiments, the time gap 244 may be provided to ensure a relaxation of the tongue 170 a selected amount, or to ensure a dissipation of the stimulation from either of the right or left stimulation lead tips 40, 44. Thus, the stimulation gap 244 may be about 0.25 seconds to about 0.75 seconds, and further including about 0.5 seconds.

Regardless of the length of the right or left stimulation portions 230, 234, the ramp up or ramp down times, or other features of the right and left stimulations, the stimulation gap 244 may separate stimulation on a right and left side of the tongue 170. Thus, the left lead 40 may be caused to stimulate only a left portion of the tongue 170 for a selected period of time, stimulation may then be stopped to the left stimulation lead 40 for a selected period of time (i.e. the stimulation gap 244), and stimulation may then be initiated by the right lead 44 for a selected period of time to stimulate only the right side. Thus, effectively, only one side of the tongue 170 is stimulated at a time. As discussed above, the stimulation pattern may then be repeated for a selected period to stimulate the tongue 170.

Figure 5B:
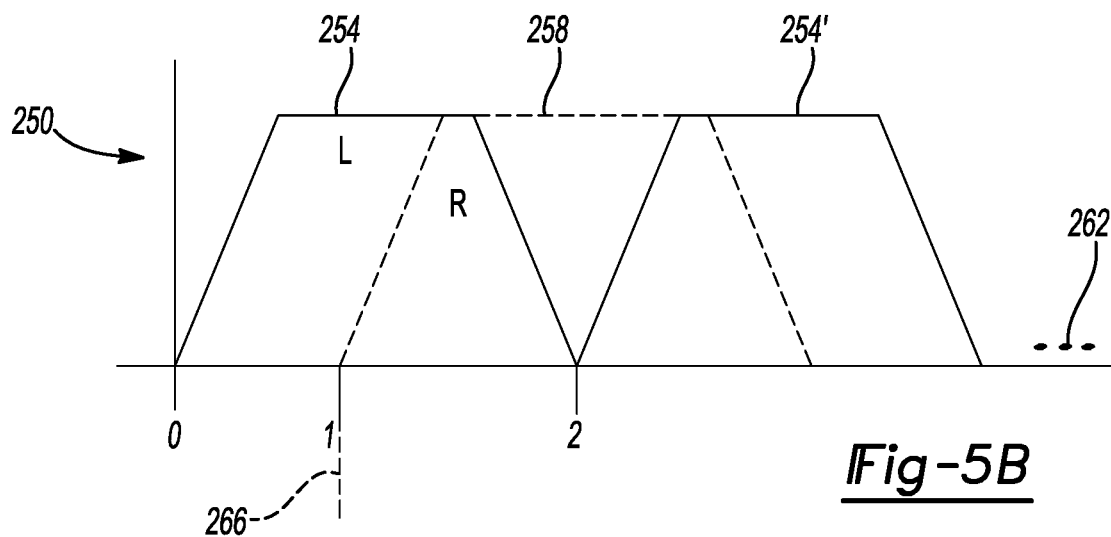

Turning reference to FIG. 5B, a graph 250 is illustrated. The graph 250 is similar to the graph 220, discussed above, and will not be discussed in detail separate from the stimulation portions, which include a left stimulation portion 254, illustrated in solid line, which may repeat, including a repeating portion 254'. Further, a right stimulation 258 is illustrated in dash line. Similarly, as discussed above, the simulation pattern may repeat including the portion illustrated in FIG. 5B along a repeating section or portion 262. Each of the stimulation portions 254, 258 may include ramp up, peak, and ramp down portions, similar to those discussed above. Accordingly, the individual portions will not be discussed as they are similar to those discussed in FIG. 5A.

The stimulation portion or sections, however, as illustrated in FIG. 5B, may be for a selected period of time, such as the first left stimulation portion may stimulate between a time zero and a time two. In various embodiments the time elapsed between zero and two may be any appropriate time, such as about 1 second, as discussed above. The right stimulation 258, however, may initiate or start at a selected time, such as a time one. The time one may be a selected time between time zero and time two. For example, the time passage or lapse between time zero and time one may be about 0.5 seconds. Therefore, the left stimulation 254 may be on for about 1 second and about half way through the right stimulation 258 may initiate. The stimulation of the left and the right, therefore, may have an overlap 266 of a selected time, such as about 0.5 seconds. Thus, while the left electrode 40 is being powered to stimulate the left portion of the tongue 170, the right electrode 44 may be initiated to stimulate the right portion of the tongue 170 simultaneously.

This allows the stimulation in the tongue 170 to be bilateral, however, include a selected simultaneous overlap 266. The overlap may occur at any appropriate time, such that the ramp up of the right stimulation 258 occurs so that the peak occurs as the left stimulation begins to ramp down. It is understood, however, that other appropriate overlaps may be provided and again the particular length of overlap may be different based upon a selected subject. Nevertheless, it is understood that the stimulation system 24 may provide stimulation that overlaps, as illustrated in FIG. 5B and/or includes a time gap, as illustrated in FIG. 5A.

Figure 5C:
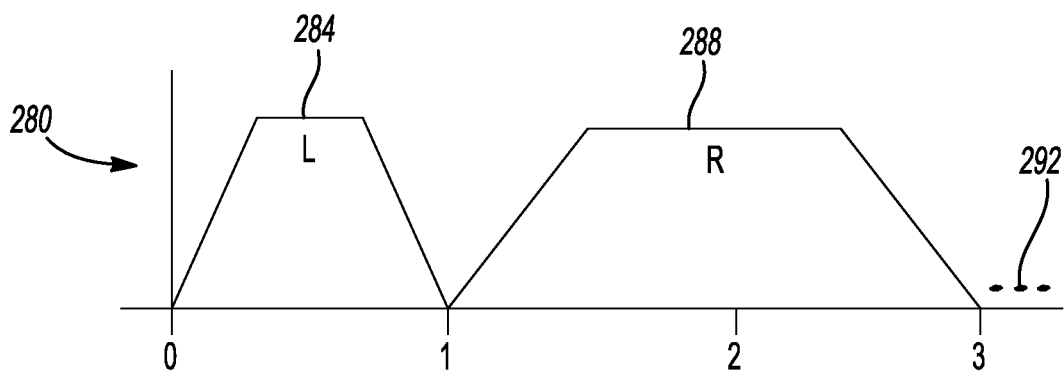

Turning reference to FIG. 5C, a graph 280 is illustrated. The graph 280 may include axes similar to those discussed above and, therefore, will not be repeated in detail here. As illustrated in the graph 280, a left stimulation 284 and a right stimulation 288 is illustrated. Again the left and right stimulations 284, 288 may include selected ramp up and ramp down and peak periods, as illustrated in the graph 280, are not repeated in detail here as they are similar to those discussed above.

The left stimulation 284 may stimulate from a time zero to a time one. The right stimulation may stimulate from the time one to a time three. As discussed above, the left stimulation 284 and the right stimulation 288 may be separated by a selected time gap 244 and/or include a selected overlap 266. It is further understood that the right stimulation 288 may begin immediately during a pause or ending of the left stimulation 284 and/or vice versa. Similarly the pattern of the left and right stimulation 284, 288 may repeat 292 for a selected time.

As illustrated in FIG. 5C, the left stimulation 284 may have a length one, which may be any appropriate time span, such as 1 second. The right stimulation 288 may include a selected time span such as two, which may be any appropriate time span, such as 2 seconds. Therefore, it is understood that the left and right stimulation periods may be different periods, such as one being twice as long than the other. It is further understood that the variance in times may alternate and/or be reversed such that the left stimulation 284 may be longer than the right stimulation 288. In this manner, the left and right stimulations 284, 288 may provide stimulations for different lengths of time to the selected portions of the tongue, such as the left HG branch 176*l* and the right HG branch 176*r*. Thus, the tongue 170 may be stimulated according to differing time lengths on the right and left side.

Figure 5D:
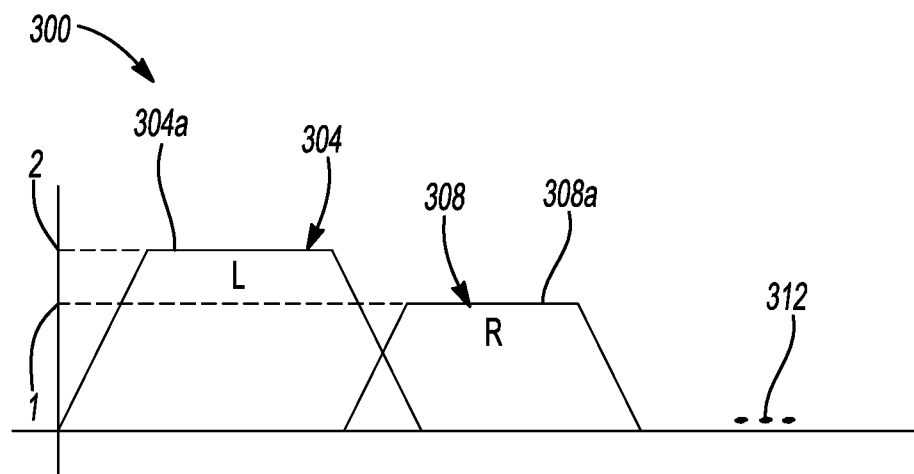

Turning reference to FIG. 5D a graph 300 is illustrated. Again, the graph 300 may be similar to the graphs discussed above, and will not be discussed in detail. As illustrated in the graph 300 a left stimulation 304 and a right stimulation 308 are illustrated. As discussed above, the stimulations may have the gap 244 between them, the overlap 266, or may be substantially start and stop when the other respectively starts or stops. Further the pattern may repeat as illustrated by the repeat symbol 312.

The left and right stimulations 304, 308, may further include different peak magnitudes. As illustrated in FIG. 5D, the left stimulation peak 304*a* may have a magnitude of two. The peak of the right stimulation 308*a* may, however, have a different magnitude, such as a magnitude of one. It is understood that the magnitude of one and the magnitude of two may represent any appropriate magnitude, such as the magnitude of one being about 1 volt and the magnitude of two being about 2 volts. The stimulation magnitude, however, may also refer to other magnitude values such as an electrical current. Nevertheless, the left and right peaks 304*a*, 308*a* may be different from one another. It is further understood that the magnitude of the left stimulation 304*a* may be less than the magnitude of the right stimulation 308*a*, and vice versa. Further, as discussed above, the magnitude may be different from one another and may also alternate in magnitude. Accordingly, after a selected period of time the left magnitude 304*a* may be less than the right magnitude 308*a* and may also switch back.

Figure 5E:
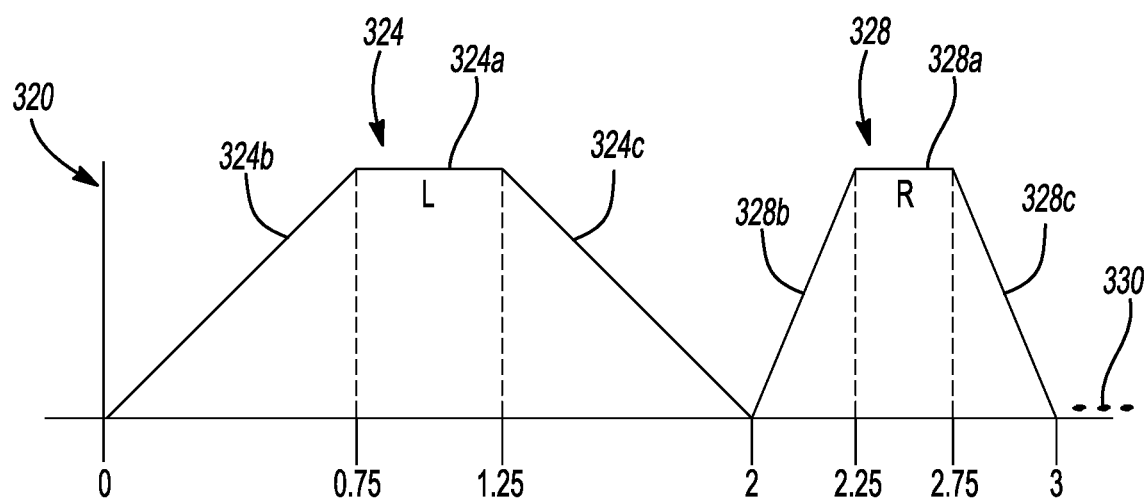

Turning reference to FIG. 5E, a graph 320 is illustrated. Again the graph 320 may be similar to the graph discussed above, and details will not be discussed here. Illustrated in the graph 320 is a left stimulation 324 and a right stimulation 328. The left stimulation 324 includes a peak stimulation magnitude 324*a* and the left stimulation includes a peak 328*a*. The peak stimulations may be of the same magnitude, or different magnitudes, as discussed above. Further the left and right stimulations 324, 328 may overlap, have a gap therebetween, or immediately follow after one another. The stimulation pattern may repeat in the stimulation repeat 330.

The left stimulation 324 may include a ramp up 324*b* and a ramp down 324*c*. Similarly the right stimulation 328 may include a right ramp up 328*b* and a ramp down 328*c*. The left stimulation 324 may begin at time zero and end at time two. The ramp up 324*b* may extend between time zero and time 0.75 and the ramp down may extend between time 1.25 and 2. Accordingly, the ramp up and ramp down 324*b*, 324*c* may have time lapses of about 0.75. It is understood that the time lapses may be any appropriate time, and may include time lapses of about 0.75 seconds, each.

The right stimulation 328 may begin at time two and have a ramp up until time 2.25. The ramp down 328*c* may have a ramp down time 2.75 to time three. Accordingly, the ramp up 328*b* and the ramp down 328*c* may have time lapses of about 0.25. It is understood that the lapsed time may be any appropriate time, and 0.25 seconds is merely exemplary. Nevertheless, the ramp up and ramp down of the right stimulation 328 may be about 0.25 seconds, while the ramp up and ramp down 324*b*, 324*c* of the left stimulation 324 may be about 0.75 seconds. The time of the peak stimulation for the left and right stimulating peaks 324, 328 may be substantially similar or identical, however, the ramp up and ramp down times may be different. It is also understood, however, that the peak times may also be different, include different amplitudes or magnitudes, or also otherwise different. Nevertheless, it is understood that the ramp up and ramp down times may differ in length and slope, as illustrated in FIG. 5E.

Figure 5F:
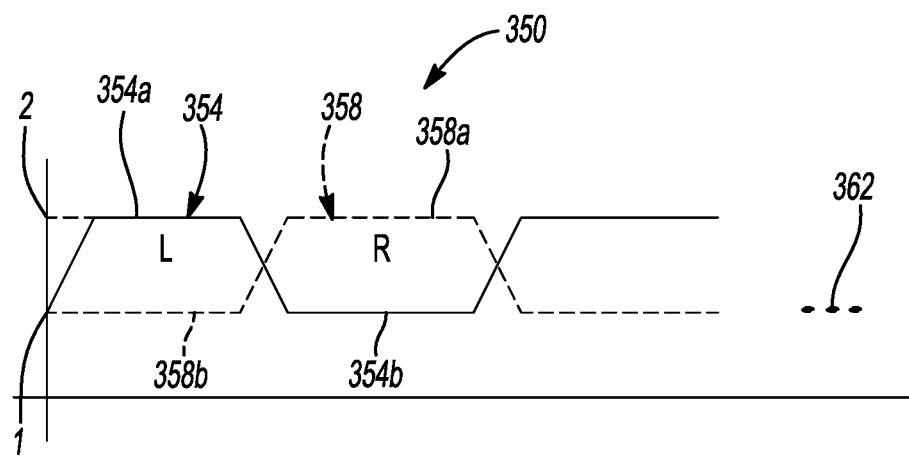

Turning reference to FIG. 5F, a graph 350 is illustrated. Again the graph 350 may include portions that are similar to those discussed above, and will not be repeated here. Further, the graph 350 illustrates a left stimulation 354 in solid lines and a right stimulation 358 in dash lines. Further the stimulation pattern may repeat as illustrated by the repeat 362. Again, it is understood, that the left stimulation 354 and the right stimulation 358 may include various features, such as those discussed above, including the gap 244, the overlap 266, a start and stop that are substantially simultaneous, and the like.

The graph 350 illustrates that the left and right stimulations 354, 358 may alternate between a maximum or peak stimulation 354*a*, 358*a* and a minimum stimulation 354*b* and 358*b*. The maximum stimulation 354*a*, 358*a* may be any appropriate magnitude, and may be substantially selected to be the same for both the left and right stimulations 354, 358. In various embodiments, the maximum or peak stimulation 354*a*, 358*a* may be a magnitude of two. The minimum stimulation 354*b*, 358*b* may be a selected magnitude such as a magnitude of one. Again as understood that the left and right stimulations 354, 358 may have respectively different maximum and minimum stimulations and the illustration of a minimum of one and a maximum of two is merely exemplary. Nevertheless, as illustrated in the graph 350, the minimum stimulation 354*b*, 358*b* need not be zero. As illustrated and discussed above, the stimulations may vary between zero and some selected magnitude. It is understood, however, that the stimulations may not return to zero during a selected stimulation period. Accordingly, during stimulation the left stimulation may alternate between one and two, after stimulation has begun, and the right stimulation 358 may also alternate between a magnitude of one and two. The stimulation provided to the tongue 170, through both of the electrode tips 40, 44, need not ever be zero during a stimulation period. Although the stimulation from either or both of the electrode tips 40, 44, may alternate and increase and decrease over time, the stimulation from either of the electrode tips need not be zero. Thus a bilateral continual stimulation may occur even if it varies over time.

Figure 5G:
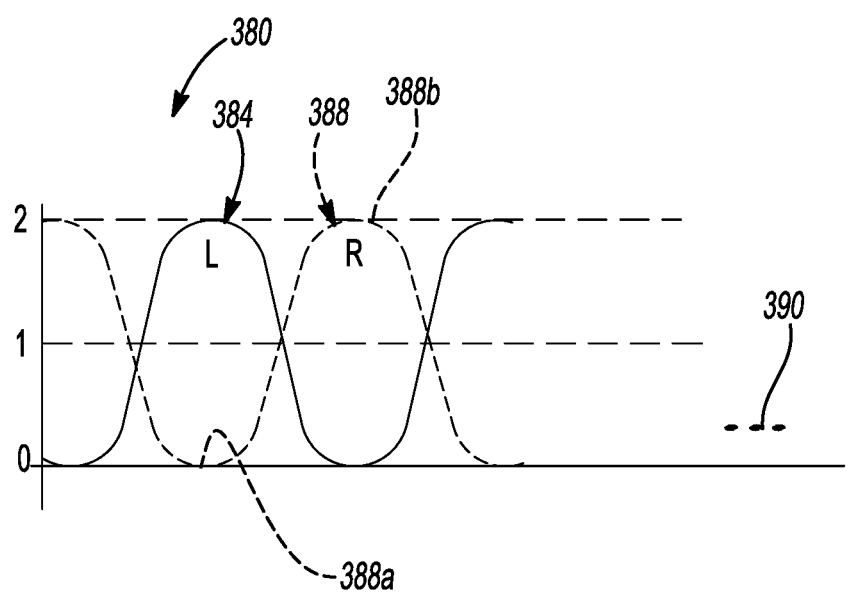

Turing to FIG. 5G, a graph 380 is illustrated. The graph 380 includes portions similar to those discussed above and will not be repeated in detail here. The graph 380 further includes a left stimulation waveform 384 illustrated in solid line, and a left simulation waveform 388 illustrated in dash line. As illustrated in FIG. 5G, the left simulation may be substantially sinusoidal between a magnitude of zero and a magnitude of two. Similarly the right stimulation 388 may alternate between a minimum 388*a* of zero and a maximum of 388*b* of two. The left and right curves 384, 388, as illustrated in FIG. 5G, may alternate in a sinusoidal fashion or manner and may cross at any selected value, such as a value magnitude of one.

The frequency, amplitude, and phase of the respective stimulation waves 384, 388 may be varied to provide a selected stimulation to the subject 62 similar to that discussed above. As illustrated in FIG. 5G, the intersection of the left and right stimulations 384, 388 may be in the magnitude of one, such that there is never a magnitude of zero stimulation to the tongue 170. It is understood, however, that the respective curves 384, 388 may be moved such that the stimulation may go to zero from both of the leads 40, 44 at a selected time and/or for a selected period of time. Nevertheless, the stimulation from the left and right leads 40, 44 may vary over time being a sinusoidal wave rather than a straight ramp up and ramp down and/or square wave, as discussed above. Thus, the peak stimulation may be provided for only a small amount of time and the stimulation is substantially constantly varying to either or both of the lead tips 40, 44. Further, as discussed above, the respective stimulation curves 384, 388 may repeat for a selected period of time 390.

With continuing reference to FIGS. 5A-5G, stimulation patterns from the ID 30 may be provided to the electrode tips 40, 44 in a plurality of waveforms, as discussed above. Further, as illustrated in FIG. 5F, the stimulation magnitude may never reach zero. However, the minimum stimulation, as illustrated to be one, may be an amount provided to at or just below (e.g. about 0.1 volts to about 15 volts) to cause stimulation and/or contraction of a selected muscle. Accordingly, while the magnitude may not be zero for the stimulation, the stimulation magnitude value may be that causes no activation of a selected muscle. Thus, the waveform of stimulation may be between a stimulation value that does not stimulate or cause contraction of muscle to a value that causes a selected contraction of the muscle.

Further, as discussed above, the waveforms of any of the selected waveforms may include a substantially square wave, where a ramp up is substantially instantaneous between a zero or selected minimum stimulation and the peak value of stimulation. The waveform for stimulation, however, may also be sinusoidal, sawtooth, triangular, etc. It is understood that the waveforms may be an appropriate form shape selected to stimulate the selected subject 52.

Further, as illustrate above, the right and left stimulation waveforms may be out of phase with one another. Thus, stimulation may be provided with only the left lead end 40 or the right lead end 44. The phase of the two waveforms am also include some overlap, but not entirely in phase.

With continuing reference to FIG. 3 and FIG. 4, and additional reference to FIGS. 6A-6C, stimulation with the selected electrode leads 34 may include stimulation between the two lead tips 40, 44, stimulation between the various electrodes on the respective tips 40, 44, in various patterns. Various exemplary patterns are discussed here, and exemplary illustrated in FIGS. 6A-6C, to illustrated various exemplary patterns. Initially, the two lead ends 40, 44 may be positioned contra-laterally in the tongue 170. In other words, the left lead end 40 may be placed near the left portion of the tongue 170 and the right lead end 44 may be placed near the right portion of the tongue 170. The lead ends 40, 44, therefore, may be spaced laterally from one another. The lead ends 40, 44, however, may be operated to provide bilateral stimulation such that the right and left sides of the tongue may be stimulated. In various embodiments, the bilateral stimulation may be simultaneous such that both sides are stimulated at the same time.

As discussed above, various waveforms or stimulations sequences may be used to stimulate the one or more portions of the tongue 170. In addition to the various waveforms, the electrodes may be operated in a various manners to provide simulation to selected areas and/or selected simulation volumes within the tongue 10. As illustrated in FIG. 6A, the electrode tips 40, 44 are placed contra-laterally in the tongue 170. Each of the electrodes 40, 44 include a plurality of electrode pads or contacts 192, 194, respectively.

In various embodiments, for example, the first electrode contact 192a may act as a cathode and the fourth electrode contact 192d may act as an anode to cause a voltage therebetween. In various embodiments, therefore, the voltage or current 400 therebetween may stimulate an area between the first electrode contact 192a and the fourth contact electrode 192d. Similarly, the electrode contact 194a may act as an anode and the fourth contact 194d may act as a cathode and a voltage 404 may be generated therebetween.

The left electrode tip 40 may be operated substantially separately from the right electrode tip 44, in various formats as discussed above. The simulation may be between the two electrode contacts 192a and 192d and in series or sequentially with the contacts 194a, 194d. Thus, stimulation will not flow between the two electrode tips 40, 44, but only between the selected electrodes and the selected electrode tips. Further a left stimulation may be only stimulating between the two electrode contacts 192a, 192d of the left electrode tip 40 and stimulation between the electrode contacts 194a, 194d of the right electrode. This allows stimulation to be provided bilaterally in series, continuously, or in any appropriate manner, as discussed above to the selected waveforms.

Turning reference to FIG. 6B, the left and right lead tips or ends 40, 44 are positioned in the tongue 170, as discussed above. The lead tips 40, 44 include the respective electrode contacts 192, 194, as also discussed above. The contacts may be used to provide varying or different stimulation to the one or more portions of the tongue 170, in addition to that illustrated in FIG. 6A. For example, the left lead tip 40 may provide a stimulation between the two contacts 192a and 192b, such as at a first time the first contact 192a having an anode and the second contact 192b may be a cathode. It is understood that these may be alternated or reversed, in various embodiments. Further, at a second time the second contact 192b may provide a stimulation 414 between the second contact 192b and the fourth contact 192d. Therefore, at a first time, stimulation may be provided between the first and second contacts 192a, 192b, and at a second time a stimulation may be provided between the second contact 192b and the fourth contact 192d.

At a third time, for the right electrode tip 44, stimulation may be provided between the first contact 194a and the second contact 194b. The stimulation 418 may be with the first contact 194a being an anode or a cathode and a second contact 194b being the opposite thereof. At a fourth time stimulation may be provided between the second contact 194b and the fourth contact 194d. The stimulation 420 may be the second contact 194b being an anode or a cathode and the fourth contact 194d being the opposite thereof.

In various embodiments, therefore, the different contacts 192, 194 may be operated as anodes or cathodes to provide stimulation at selected areas. For example, an area stimulated by the first stimulation portion 410 or the third stimulation portion 418 may be proximal along the lead tips 40, 44, while the second four simulations 414, 420 may be more distal. In various embodiments, stimulating different areas may achieve different results relative to the subject 62.

Further, the different stimulations 410, 414, 418, 420, may be provided at different times, as discussed further herein. For example, the left electrode tip 410 may cause the stimulation 410 at a first time, which is then followed by the stimulation 420 by the right electrode tip 44, which is then followed by any other appropriate stimulation, such as the stimulation 414 with the left electrode tip 40 and/or the right stimulation tip 44 causing the stimulation 418. Further, bilateral or simultaneous stimulation of both the left and right electrode tips 40, 44 may be caused at different positions such as a simultaneous stimulation with the stimulation 410 and the stimulation 420 with the respective left and right electrode tips 40, 44.

Turning reference to FIG. 6C the left and right electrode tips 40, 44 may be positioned within the tongue 170, as discussed above. The respective electrode tips or ends 40, 44 include the respective electrodes 192, 194, as discussed above. The stimulation may be provided, according to various embodiments, between the separated left and right electrodes 40, 44. For example, the first electrode 192a of the left electrode tip 44 may provide a stimulation path with the first electrode 194a of the right electrode tip 44 along a stimulation path 430. Thus, stimulation may occur between the left and right lead tips 40, 44.

As a further example, stimulation may occur between electrode contacts at different contacts along the length of the electrode or lead tips 40, 44. For example, stimulation may occur between the second electrode contact 192b and the fourth electrode contact 194d. The stimulation path 434 may allow for stimulation between two levels or at varying distances relative to a proximal position of the electrode leads 40, 44 within the subject 62. Thus, stimulation may be provided across the tongue 170 between the two separated lead ends 40, 44.

With reference to FIGS. 6A-6C, stimulation may be provided between various electrodes of the electrode lead tips 40, 44, at various times. It is understood that the stimulation pattern may occur or change over time, such as based upon a programming of the ID 30. Thus, the subject 62 may be stimulated in an appropriate physical location, and the illustrations or examples in FIGS. 6A-6D are merely exemplary. It is understood that stimulation may be provided between any selected electrodes of the electrode lead tips 40, 44 and the above are merely exemplary regarding the stimulation between different electrode contacts 192, 194 of the respective lead tips 40, 44, and/or between the electrode lead tips 40, 44.

As illustrated in FIGS. 6A-6C the lead ends 40, 44 that are placed in different locations within the tongue may be operated to stimulated different areas within the tongue 170. The electrodes 190, 194 of the respective lead ends 40, 44 may be used to stimulated separated and different physical locations of the tongue. Different physical locations may provide differing efficacy of treatment for OSA and/or UARS.

With additional reference to FIGS. 5A-5G, stimulation from the ID 30 to the subject 62 may also occur according to selected pulses and/or waves that various stimulation of the subject 62. The various stimulation wave patterns, as illustrated in FIGS. 5A-5G, are also understood by one skilled in the art to be merely exemplary. The wave patterns may allow for stimulation of the subject according to various magnitudes, time differentials, and differentials between a left and right electrode positions. It is also understood that more than two electrode tips may be positioned in the subject such that an additional or third and/or any appropriate number of electrode positions may be determined or placed.

With reference to FIGS. 5A-5G and FIGS. 6A-6C, the subject 62, therefore, may be stimulated in a manner to reduce or eliminate muscle fatigue over an extended stimulation therapy. The reduced fatigue may increase an efficacy of treatment and/or achieve a threshold of efficacy or result parameters. For example, the waveform of stimulation may be altered or changed or waveform may alternate in a selected pattern or differential to ensure that a continuous stimulation at a single magnitude is not maintained. Thus, the stimulation may be discontinuous and allow for a period of relaxation of the muscle of the subject so that the muscle does not fatigue and no longer respond to the stimulation therapy. Further the physical location of the therapy may differ over time, as exemplary illustrated in FIGS. 6A-6C, to also assist in reducing or eliminating muscle fatigue. The fatigue of a muscle may occur when a single muscle and/or single area of a muscle is stimulated for an extended period of time. After the extended period of stimulation the muscle may no longer react or fail to contract in a selected manner. Therefore allowing a muscle to relax allows for a more and/or predictable response to a stimulation from the ID 30.

In various embodiments, therefore, as discussed further herein, stimulation may be provided to the subject 62 in a selected manner to substantially reduce and/or eliminate muscle fatigue. Reduction and/or elimination of muscle fatigue can allow for a selected result and/or optimal result for a selected subject 62. As discussed above, stimulation of one or more portions of the tongue 170 may cause activation (e.g. contraction) of selected muscles of the lingual muscle or tongue 170 to assist in treating OAS and/or UARS.

As discussed above, the stimulation may be provided to the subject 62, particularly in the tongue, for alleviating various conditions and/or providing therapy to the subject 62. The therapy may be provided to the subject according to selected electrode stimulation patterns, wave patterns for stimulation, and other features or treatment types or magnitudes. As discussed further herein, the therapy may be delivered to the subject 62 in an appropriate manner that may be based upon various factors and/or inputs from various sensors, the subject 62, a clinician, or other appropriate inputs. The therapy may be provided by the ID 30 based upon programming stored in the memory thereof, from the CTM 70, 74, or other appropriate processor. In various embodiments, the therapy may be provided based upon a set or selected set of instructions, a selection from a plurality of a set of instructions, and/or an adaptive or learning algorithm (e.g. machine learning algorithm or system) to provide a selected or optimal therapy for the subject 62.

The stimulation system 20 may include the ID 30 that provides energy to the stimulating lead tips 40, 44 according to the appropriate patterns and configurations, as discussed above. In addition to the CTM's 70, 74, the input sensors 61, 61' may provide input to the ID 30 and/or the CTM's 70, 74. As discussed above, the sensors 61, 61' may provide information regarding the subject 62 including various oxygen saturation amounts (arterial or tissue oxygenation saturation amounts), muscle activation (e.g. electromyography (EMG)), temperature, body position (e.g. using an accelerometer), cardiac rhythm (electrocardiograph (ECG)), or other appropriate sensors. As is generally understood by one skilled in the art, a sleep study may be performed on the patient which includes sensing various features of the subject 62 in a polysomnograph. One or more of the sensed elements of the subject 62 may be sensed with the sensors 61, 61' to assist in providing an appropriate stimulation to the subject 62 as a part of the therapy provided to the subject 62.

Figure 7:
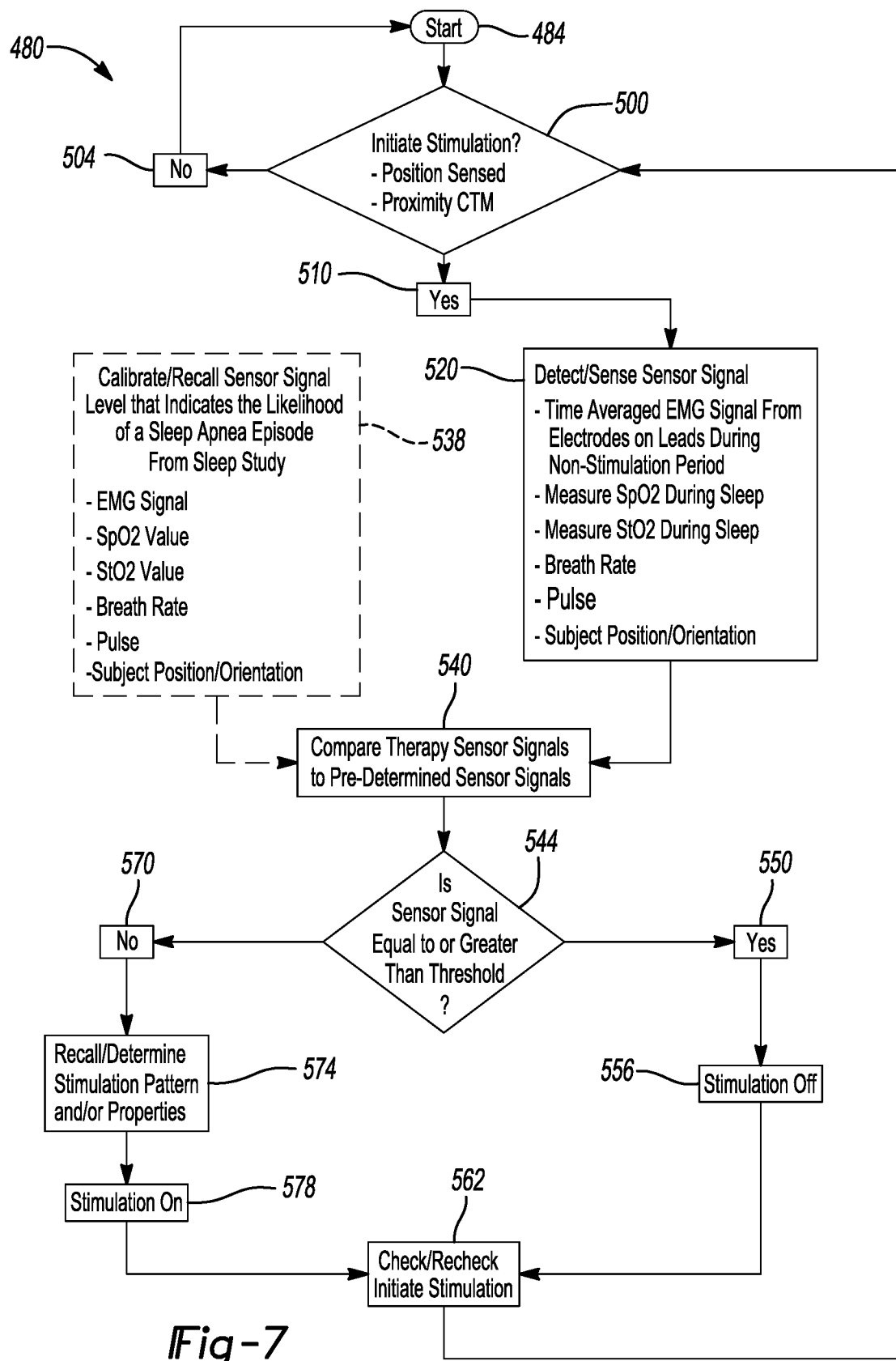
FIG. 7 is a flowchart illustrating a stimulation system use/training/testing, according to various embodiments.

Accordingly, with reference to FIG. 7 and continuing reference to FIGS. 1-6C, a process or a system flowchart 480 is illustrated. The process 480 may be executed by the processor module 50 in the ID 30, and/or the processor modules in either the first or second CTM 70, 74 via transmission of a signal to the ID 30. Accordingly, the process 480 may be used to provide a selected therapy to the subject 62, in a selected manner, as discussed above. Initially, the process 480 may begin in start block 484. The process starting in block 484 may be any appropriate start, such as powering the ID 30 on, implantation of the ID 30, or the like. Once the process is started in block 484, a determination of whether stimulation should be initiated may be made in block 500.

Initiating of stimulation may be based upon various inputs such as a determination of a proximity to one or more of the CTM's 70, 74. For example, the first CTM 70 may be positioned near a subject sleeping orientation and/or powered on or initiated by the subject 62 at the beginning of a sleep cycle. Therefore, proximity to the CTM 70 and/or receiving a signal from the CTM 70 may be provided to initiate stimulation in block 500. Further, as discussed above, various inputs from sensors, such as the sensor 61 or the external sensor 61' may be used to determine whether initiation of stimulation may occur. For example, position of the subject 62 may be used to determine that the subject 62 is in a laying position or horizontal position. Thus, the initiation of stimulation or stimulation process may be based upon the position of the subject. Regardless, initiation of stimulation may be determined in block 500.

If it is determined that initiation of stimulation should not occur, a NO path 504 may be followed. The NO path 504 may return to the start block 484. In various embodiments, for example, the determination of whether initiation of stimulation should occur in block 500 may be based upon a selected periodic cycle of the ID 30. In various embodiments, for example, a low power clock or timer may be included in the ID 30. The timer may be set for a selected period of time (e.g. 10 minutes). Accordingly, the start block 484 may be initiated every 10 minutes if the ID 30 is not already in a stimulation cycle. It is understood, however, that the start block 484 may be entered in any appropriate manner.

If initiation of stimulation is determined in block 500, a YES path 510 may be followed. The YES path 510 may go or follow to detect or sense a sensor signal in block 520. The detection of a sensor signal in block 520 may be an input from a sensor sensing any appropriate feature of the subject 62. For example, measuring of an arterial oxygen saturation (SPO2) may be made and/or the measurement of a tissue oxygen saturation (STO2). The oxygen saturation may be measured in any appropriate location, such as at the ID 30, with an external measuring device, or at any position along the lead 34. Regardless the sensor may provide a selected oxygenation saturation to the processor, such as the ID processor 50.

Other sensor information may be related to the EMG. The EMG may be sensed at the lead contact at the lead tips 40, 44. In various embodiments, for example, a chin EMG may be measured using the tip electrodes 40, 44. The EMG may be a time average signal (e.g. an EMG averaged over a selected period of time, such as 10 seconds). Regardless, the EMG may be sensed and analyzed for determination of a stimulation, as discussed further herein.

As discussed above, the subject 62 may have undergone a sleep study at a selected period of time, such as prior to implantation of the ID 30. The sleep study of the subject 62 may be used to determine various selected threshold values of sensed information of the subject 62. As discussed further herein, selected population values may be determined for sensed information such as oxygen saturation, EMG signal values, and the like. Regardless of the timing of the determination and/or source of the determination, the memory 54, and/or any appropriate memory, such as the memory 102 of the CTM 70, may be used to store for recall the selected values.

The calibration and/or recall of the selected sensor information can be made at any appropriate time, such as at an initial implantation of the ID 30, during a sleep study of the patient 62, or after initial implantation and use of the ID 30 after a selected number of sleep cycles with the ID 30 in the subject 62. Regardless, the appropriate or selected sensory levels or values may be determined and/or stored on the memory 54 for recall by the processor 50 of the ID 30.

The selected processor module, such as the processor module 50 of the ID 30, may then compare the detected sensor signal from block 520 and the calibrated or recalled value from block 538 in block 540. The comparison in block 540 may be based upon the selected sensor signal from block 520 compared to the recalled signal or value in block 538. The comparison may then be used to determine whether stimulation may be provided or should be provided to the subject 62, such as based upon the calibrated or determined value in block 538.

The calibrated signal may be based upon or used to determine a threshold value for one or more of the sensed values, such as an oxygenation value, EMG value, or the like. Accordingly, once the comparison is made in block 540, a determination of whether the sensor signal from block 520 is at a threshold or selected value when compared to the calibrated value is made in block 538. The determination is made in block 544. The comparison may be made by the processor module 50 in the ID 30 to determine whether a stimulation should be delivered to the subject 62.

The determination of whether the sensor signal is equal to or greater than a threshold in block 544 may then be made to follow a selected path. If a sensor signal from block 520, when compared in block 540, is equal to or greater than a threshold value, a YES path 550 may be followed. The YES path 550 may follow or allow for a determination that stimulation should not be on, therefore a stimulation off 556 is followed. The stimulation off in block 556 may be made to determine that no stimulation should be provided through the selected electrode leads 34. Accordingly, no stimulation or a stimulation off may include sensation or stopping of a previous stimulation or not initiating stimulation through the leads 34.

After a determination that a stimulation should be off in block 586 a check or recheck of whether stimulation should be initiated may be made in block 562. The rechecking or checking of initiation of a stimulation in block 562 may return to the initiation stimulation in block 500. Accordingly, it is understood that the process 480 may be a loop process once the ID 30 is started or implanted in block 584. Accordingly, the initiation of the stimulation in block 500 may continue through the various steps to the determination of whether the sensor signal is equal to or greater than a threshold in block 544, as discussed above.

Therefore, a determination of whether the sensor signal is equal to or greater than a threshold in block 544 may also follow a NO path in block 570. Once following the NO path in block 570, a determination or recall of stimulation pattern or properties is made in block 574.

The stimulation pattern or properties may be any appropriate stimulation pattern or properties, as discussed above. The pattern may be preprogrammed in the memory 54 of the ID 30 at any appropriate time, such as based upon a sleep study of the subject 62, a learning based upon a selected learning algorithm, as discussed further herein, or other appropriate determination. Regardless, a recall or determination of a stimulation pattern may be made in block 574 to stimulate the subject 62.

After a recall or determination of a stimulation pattern or property in block 574, the stimulation may be turned on or started in block 578. As discussed above, the stimulation may not be provided from the ID 30 to the subject 62 through the leads 34 until a selected determination is made, such as the determination in block 544. Accordingly, once the determination is made that a threshold value of a selected sensor input is not made in block 544, the NO path 570 is followed and a determination or recall of the stimulation pattern in block 574 is made. The stimulation recalled in block 574 may then be initiated or started in block 578 to stimulate the subject 62 according to a determined or selected stimulation pattern.

After starting stimulation, the subject 62 may be stimulated for an appropriate period of time (e.g. one selected in the determined stimulation pattern). Once the selected stimulation occurs in block 578 a check or recheck of when initiation of stimulation should be made in block 562 may occur. Accordingly, even after a stimulation occurs in block 578, a recheck or loop of the stimulation determination may be made according to the process 480. Thus, the process 480 may be substantially continuous or a loop process to provide stimulation to the subject 62 as needed and/or determined to provide an appropriate therapy to the subject 62.

The process 480 may allow for a stimulating or not stimulating the subject 62. The process 480 may loop an appropriate number of times, according to the process 480, to provide therapy to the subject 62. The therapy to the subject 62, therefore, may be made by the ID 30 according to the process 480 based upon a selected calibrated or determined sensor signal level or value for various sensor inputs, as discussed above. The stimulation may then be turned on or turned off based upon a comparison of sensed values to the calibrated or determined recalled values, such as in determination block 544.

Figure 8:
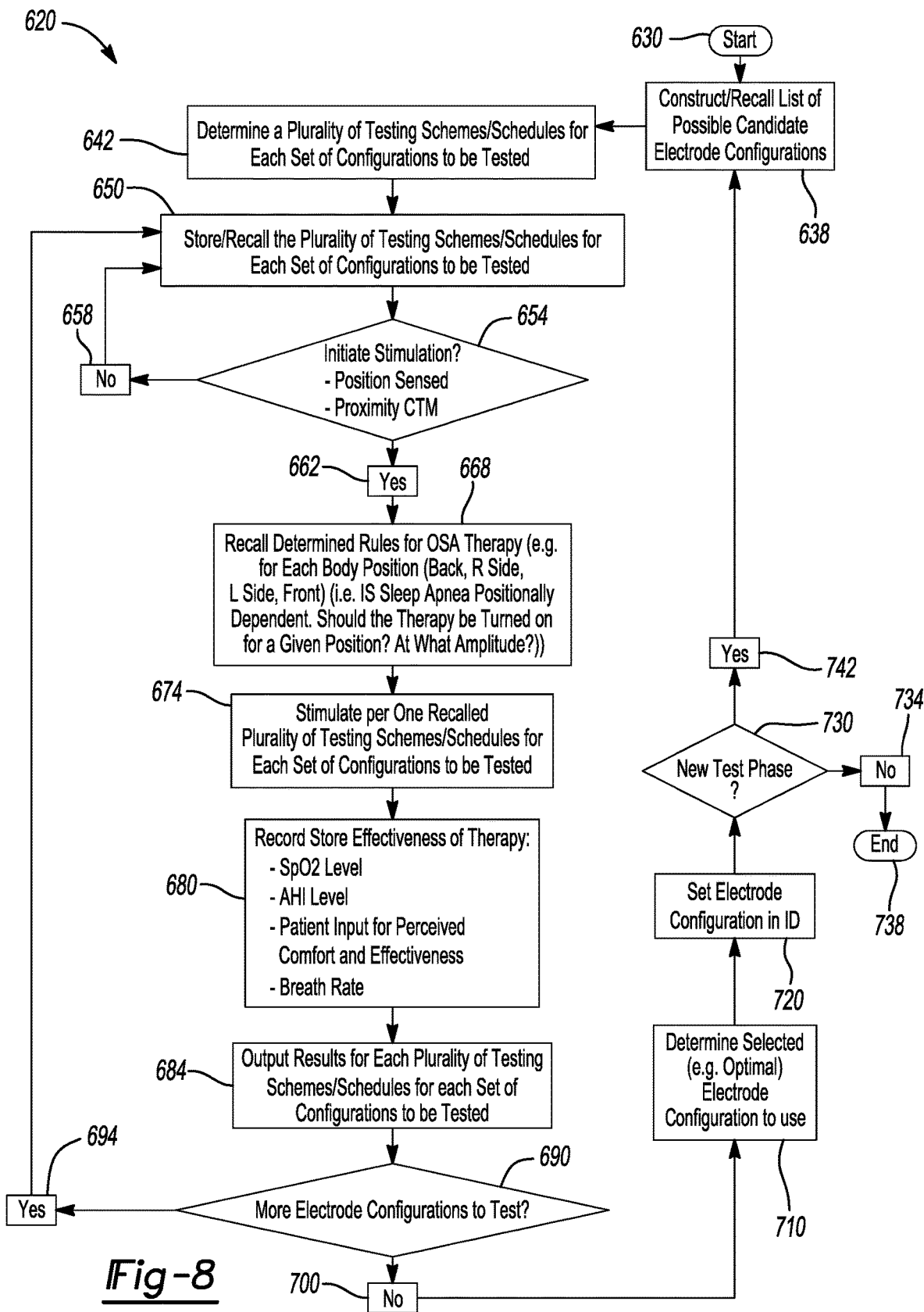
FIG. 8 is a flowchart illustrating a stimulation system use/training/testing, according to various embodiments.

With continuing reference to FIGS. 6A-6C, and additional reference to FIG. 8, a process for allowing the determination of a selected or appropriate stimulation pattern for the subject 62 (e.g. including an optimal or selected optimal configuration), may be made. The configuration of the stimulation may be made or tested based upon a plurality of different configurations.

As illustrated in FIGS. 6A-6C, exemplary configurations of stimulation between one or more of the contacts 192, 194 of the electrode ends 40, 44, may be made. A selected list of all possible configurations and/or selected configurations may be determined. The selected or possible configurations, thereafter, may be tested on the subject 62 to assist in determining an optimal or selected optimal stimulation configuration.

Accordingly, with reference to FIG. 8, a testing and/or stimulation process 620 is illustrated. The process 620 may be a stimulation or electrode configuration stimulation testing process. The process 620 may start in start block 630. After the start block 630, such as after implantation of the ID 30 into the subject 62 and/or selection of implantation (e.g. prior to a procedure), a construction or recall list of possible candidate electrode configurations may be made in block 638. The list of possible electrode configurations for stimulation may include those exemplary illustrated in FIG. 6A, FIG. 6B, and FIG. 6C. Further, it is understood, that additional stimulation configurations may be made or determined and may be included in the list in block 638.

Accordingly, the exemplary configurations discussed above are not intended to be a limit of possible stimulation configurations to the subject 62.

Following the construction or recall of the list of possible configurations, a determination of a plurality of testing schemes may be made and/or is scheduled for each set of configurations to be tested in block 642. The schedule of testing may be made based upon the list, and may be set for a number of hours, days, sleep cycles, or the like. For example, the configuration as illustrated in FIG. 6A may be determined to be tested first, followed by the configuration illustrated in FIG. 6B, followed by the configuration illustrated in FIG. 6C. It may be determined to test each configuration for a selected number of sleep cycles, a selected number of sleep hours, or any other appropriate time. Further the testing configurations may be scheduled for a period after implantation, such as beginning a testing period after a certain number of sleep cycles, sleep hours, or the like. Nevertheless, a selected schedule may be determined.

Following the determination of the testing schedule a storage of the testing schedule may be made in block 650. The storing in block 650 may be storing the test schedule, including the configurations, in an appropriate memory, such as the memory module 54 of the ID 30. It is understood that the testing schedule may also be stored in any appropriate memory, such as the memory 102 of the CTM 70. As discussed above the CTM 70 may transmit a signal to the ID 30 to be executed thereby (e.g. the CTM 70 transmits instructions to the ID 30 to be executed by the processor 50). Thus, the configurations and testing schedule may be stored in any appropriate memory to be executed by the ID 30.

After storing the schedule in block 650, a determination of whether stimulation should be initiated in block 654 may be made. The determination of initiation of stimulation may be based on appropriate or selected input including a determined or sensed position of the subject 62, an input of the CTM 70, a proximity to the CTM 70, or other appropriate inputs. The initiation of stimulation may be similar to that discussed above, such as in the process 480.

If initiation of stimulation is not determined to be appropriate in block 654, a NO path 658 may be followed to return to the stored recall of the testing schedule in block 650. Thus, the initiation of stimulation may be used to determine or create a loop to allow for recall at appropriate stimulation schedules, such as a testing schedule, to be performed of an ID 30. The determination of whether stimulation should occur may be looped to ensure that the stimulation schedule is maintained or determined over an appropriate period of time.

If initiation of a stimulation is determined to be proper, a YES path 662 may be followed to recall or access determined rules for therapy in block 668. The recalled rules for therapy may be similar to those discussed above, including initiating a particular therapy based upon various inputs and/or sensor signals. Accordingly, sensor signals may include a position of the ID 30 and/or various other sensor inputs such as an EMG, oxygen saturation, or the like. Nevertheless, the therapy may be provided from the ID 30 according to the rules recalled in block 668. Accordingly, the rules 668 may be included in instructions that are stored in the memory module 54 that may be executed by the processor module 50 by the ID 30.

The stimulation, once initiated in block 654, and following the rules or instructions as recalled in block 668, may be stimulated according to one of the selected schedules or configurations in block 674. As discussed above, a plurality of configurations may be stored in block 650. Accordingly, during a testing or configuration phase, such as during the process 620, a selected one of the stimulation configurations may be made in block 674 for testing or stimulating the subject 62. Thus, for example, during a first testing period the configuration is illustrated in FIG. 6A may be sued to stimulate the subject according to the rule recalled in block 668.

During stimulation according to a selected one of the plurality of stored configurations, as selected in block 674, a record of effectiveness of the therapy may be made in block 680. The record may be based upon various sensors incorporated or included with the ID 30, worn by the subject 62, (e.g. the external sensor 61'), or other appropriate sensors related to the ID 30. In various embodiments, for example, oxygenation saturation may be sensed, a breath rate may be sensed, or other appropriate information may be sensed and stored with the ID 30. As discussed above, the CTM 70 may also be provided for user access by the subject 62. The subject 62 may enter or provide feedback regarding a selected sleep cycle which may be related to a selected one of the tests selected or used to stimulate the subject in block 674. Accordingly, the subject may input information regarding perceived comfort, sleep effectiveness, or other appropriate information. Further, various additional sensors may be provided that may provide input or sense the subject 62 during a selected period.

The information recorded in block 680 may be stored in any appropriate memory, such as the memory module 54, the memory module 102, and/or other appropriate memory module. At a selected time, the information may be recalled for further determination and/or analysis. Nevertheless, the various sensors may record and/or store information regarding the sensed parameters of the subject 62 and/or the subject 62 may input information regarding the sleep.

The recorded information may then be output for a selected analysis in block 684. The output may be transferred to the CTM 70, the CTM 74, or other appropriate systems. Nevertheless, the output may be stored for further analysis, such as after a selected number of sleep cycles. The various memory modules may include capacity to store an appropriate amount of sensor data and/or user input data for further analysis.

After output of the results in block 684, and/or storage of the results in block 680, a determination of whether more electrode configurations are to be tested may be made in block 690. If further configurations are to be tested, a YES path 694 may be followed to determine whether initiation of stimulation should occur in block 654. As discussed above, a plurality of electrode configurations may be made, such as the configuration of FIG. 6B and/or the configuration in FIG. 6C and/or other additional configurations. The decision block 690 may be used to determine whether additional configurations of the electrodes have been included in a list of possible electrode configurations for testing. It is understood, as discussed above, that any appropriate number of electrode configurations may be stored for testing on the subject 62.

If a determination is made in block 690 that additional configurations of electrodes is not to be tested, a NO path 700 may be followed. In following the NO path 700, a determination of whether a selected configuration is to be used and/or a selected configuration is an optimal configuration may be made in block 710. A determination of a selected configuration may be selecting a configuration that achieves a selected or optimal result for the subject 62. As discussed above various sensors may be used to sense the subject 62. For example, a breath rate and/or oxygenation saturation may be measured of the subject 62. Accordingly, a stimulation configuration that achieves a selected or most optimal sensor recording or rating of selected sensor outputs may be used or determined to be an optimal configuration for the subject 62. For example, a blood oxygenation saturation level may be weighted as the factor most relevant. Accordingly, the electrode configuration that achieves the highest average, highest optimal, or other appropriate threshold level of oxygenation saturation may be used or related to a particular configuration of the electrodes and this configuration may be determined to be the optimal or selected for the subject in block 710. The selection in block 710 may be based upon an efficacy of the therapy for the subject 62. The efficacy may be based on achieving selected or threshold sensor values.

In various embodiments, the selected sensor readings may be based on the single subject or a population. For example, Oxygen saturation levels may be selected to be read at or near about or above about 95% and selected to be maintained or sensed above at least about 90% for selected sleep periods. A normal or selected therapy respiration rate for an adult may be about 12 to 20 breaths per minute. A heart rate may be selected to be achieved or therapy may be provided to maintain about 40 to about 100 beats per minute (BPM) during sleep. Also, combinations of sensor readings may be used such as coupling a drop in oxygen level along with an arousal (registered by accelerometer measuring movement) may also be an alert that insufficient stimulation is being delivered meant to avoid apnea/hypopnea. One or more sensor inputs may be used to consider quality of sleep optimization with requisite feedback sensors (e.g. EEG, etc.).

The selected or optimal configuration in block 710 may be made or based on a determination of an efficacy of the treatment including the stimulation therapy based on the output results from block 684. The determination of the optimal electrode configuration made in block 710 may be made based on the efficacy. The efficacy may be based on or determined as a comparison of the data values in block 680 to a predetermined value threshold and/or a subject threshold or response. For example, a threshold may be determined for oxygenation. The stored value in block 680 and output in block 684 may be compared to a predetermined oxygenation threshold. An efficacy (e.g. efficacy value) may be determined based on whether the predetermined threshold is achieved or exceeded and by what amount. Thus, a more or greater efficacious therapy may include an electrode configuration that achieves a greater oxygenation than another configuration. It is understood, however, that efficacy may be based upon more than one value (e.g. sensor value) and/or weights of different parameters.

Thresholds may be those that are outside normal or selected ranges, as noted above. Selected thresholds may also be subject specific and calibrated and stored for each subject. For example, if blood oxygen levels are below about 95. No standard or lack of movement during sleep as registered by the position sensor (e.g. an accelerometer). No or lack of normal chest excursion. For example, a position sensor in/on a chest of a subject could register excursion/ movement and if the chest stops moving for 10 seconds (i.e. possible apnea event) then that could be avoided by stimulating or increasing or initiating stimulation.

Once a determined optimal configuration is made in block 710, the ID 30 may be set to this configuration in block 720. Accordingly, for example, the ID 30 may be implanted with a set of test configurations. The set of test configurations that are recalled in block 650 may then be tested in the subject 62 over a selected period of time, according to the process 620. After a determination of an optimal or selected configuration is made in block 710, the ID 30 may be set with the selected configuration in block 720. Thus the subject 62 may experience therapy according to the selected configuration of the electrodes set in the ID in block 720.

The electrode configuration may be set in block 720 at any selected time. For example, as noted above, the process 620 may be selected to run for a set period of time. It is understood, however, that the determination in block 710 may be substantially in real time. For example, the processor 50 may receive inputs and determine a selected threshold is not met (e.g. oxygenation). If a threshold is not met, the processor may recall a different electrode configuration from block 650 for stimulation. Thus, the process 620 may allow for substantially real time (e.g. once or more during a current or single sleep cycle) determination and stimulation with an electrode configuration.

The process 620 may further include a determination of whether a new test phase is to occur in block 730. A new test phase may occur at any appropriate period based upon a selected signal. For example, after a three month time period, a selected number of sleep cycles, or the like, a new test phase may be made in block 730. One or more of the CTM's 70, 74 may be used to initiate a new test phase in the ID or determination block 730. Accordingly, the process 620 may be used to test a selected number of configurations at any appropriate time. Further, it is understood, that the CTM's 70, 74 may be used to transmit further configurations to the ID 30 for additional testing.

If no additional testing is to be performed, a NO path 734 may be followed to end the process in block 738. The process 620, however, may be re-initiated at any appropriate time, according to the processes discussed above.

Further, if a new test phase is determined in block 730, a YES path 742 may be followed to determine whether initiation of stimulation should be made in block 654. Accordingly, for example, the subject 62 may have a visit with a clinician at a selected time and the clinician may determine that an additional test phase should be performed. The clinician may initiate a new test phase with the CTM 74 by transmitting a signal to the ID 30. The ID 30 may then determine the that a new test phase should occur in block 730 and the YES path 742 may be followed to determine whether initiation of stimulation should occur in block 654. Accordingly, even if the subject 62 visits a clinician during a non-sleep period, the clinician may initiate a new test phase in block 730 and the test phase may reinitiate by following the YES path 742.

As discussed above, processes and methods may be used to operate and/or determine a selected or optimal operation with ID 30, e.g. waveform for stimulation, for therapy to be provided to the subject 62. Accordingly, with reference to FIGS. 5A-5G, and additional reference to FIG. 9, a process or method 820 is illustrated. The process 820, as discussed further herein, may be used to determine or select an appropriate stimulation waveform pattern to be provided to the subject. For example, as illustrated in FIG. 8, the process 620 may be used to determine or select a selected (e.g. optimal) configuration for stimulation of the electrode provided on the electrode tips 40, 44. In addition, and/or alternatively thereto, a stimulation wave pattern may also be tested and/or selected for the subject 62. As illustrated in FIGS. 5A-5G, exemplary stimulation wave patterns may be provided by the ID 30. Accordingly, the process 820 may be used to determine (e.g. test) and/or select a wave pattern that may be optimal for the subject 62 to provide an appropriate or selected therapy thereto.

Figure 9:
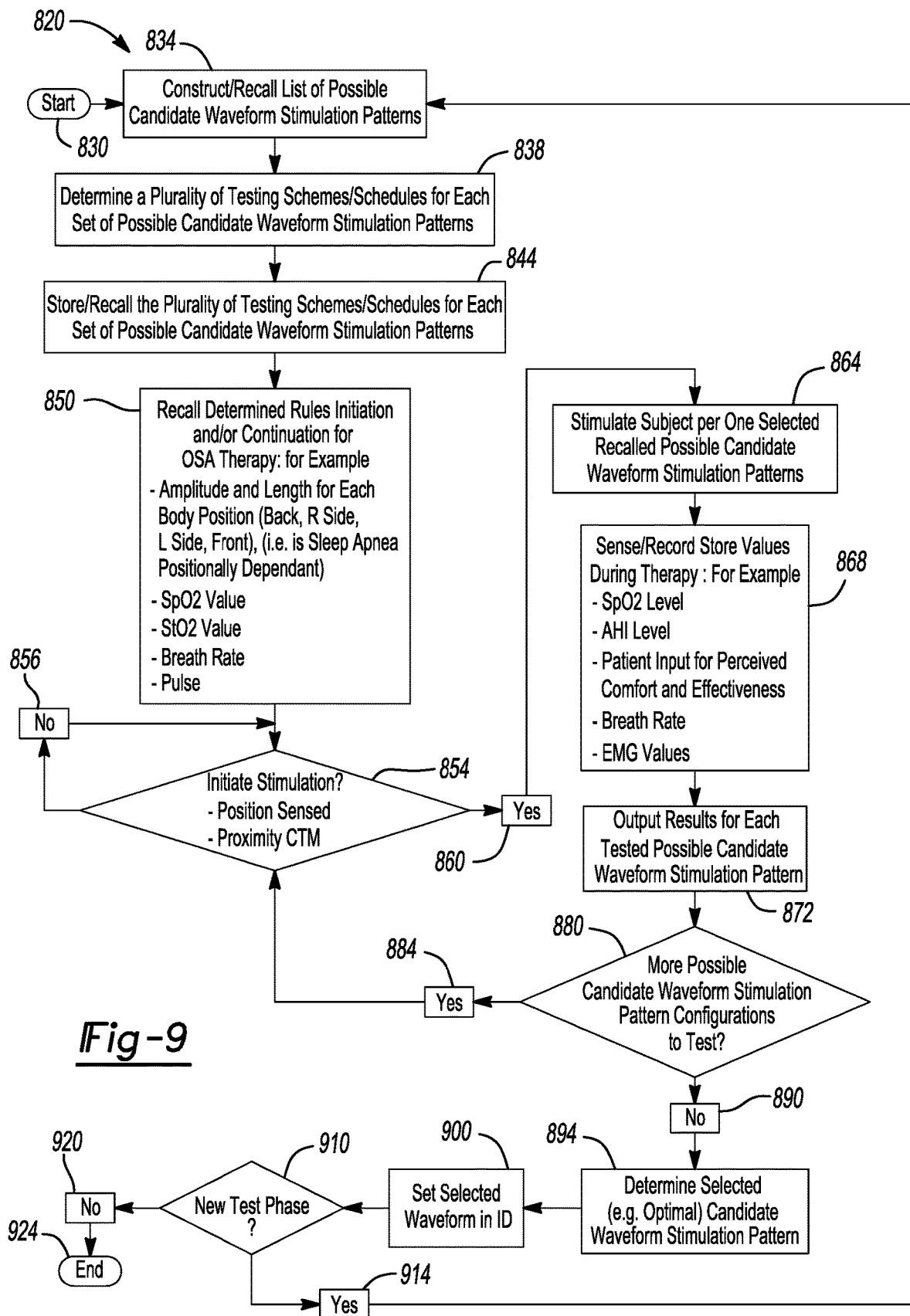
FIG. 9 is a flowchart illustrating a stimulation system use/training/testing, according to various embodiments.

With reference to FIG. 9, therefore, the process 820 is illustrated. The process 820 may begin at start block 830. The start block 830 may be any appropriate start, as discussed above, including selecting the ID 30, implanting the ID 30, initiating (e.g. powering and selecting an initial start period), or other appropriate configuration of the ID 30. Following the initiation of the start block 830, and/or at the appropriate time, a selected list or possible waveforms may be determined in block 834. The waveforms constructed or determined may include those, as discussed above, including those illustrated in FIGS. 5A-5G. The waveforms may include the stimulation time, overlap of stimulation, amplitude of stimulation, period of stimulation, or other appropriate waveforms. As discussed above, the waveforms may include more than those illustrated in FIGS. 5A-5G and the particular waveforms are provided merely for illustration. Thus, the ID 30 may be used to provide stimulation to the subject in an appropriate manner according to various waveforms or types of stimulation, as discussed above. The list of selected waveforms may include any appropriate or all possible waveforms provided by the device, or lists selected by the user 62, clinician, or other appropriate individual.

Once the list of possible waveform patterns is determined in block 834, a testing schedule for each of the waveforms may be made in block 838. The testing schedule, similar to the testing schedule in block 642 discussed above, may include a length test including a number of sleep cycles, a number of days, or the like. The testing pattern may allow for determination or selection of a number of data points to be collected for each of the possible or selected sleep stimulation patterns as determined in block 834.

Once the schedule is determined by block 838 of the various patterns from 834, the testing scheme schedule may be stored in block 844. The storage of the testing scheme may include storage of the particular patterns from block 834, the schedule from block 838, or other appropriate considerations. Further the storage in block 844 may be stored into any appropriate memory module, such as the memory module 54 of the ID 30, the memory module 102 of the CTM 70, or other appropriate memory module. Regardless the testing scheme may be recalled at an appropriate time, for testing and operation of the ID 30 according to the appropriate manner.

Once the testing scheme has been stored and provided for recall during a selected testing phase, a recall of determined rules for initiation and/or continuation of stimulation may be made in block 850. The determined rules for initiation and/or continuation of the therapy (e.g. therapy for OSA and/or UARS) may be stored in an appropriate memory module, such as the memory module 54 of the ID 30. As discussed above the rules may include when and how to initiate OSA therapy, intensity, or the like. As illustrated in the process 820, however, the various stimulation patterns may be tested therein, and the rules recalled the block 850 may include general rules regarding initiation of stimulation therapy and/or appropriate configuration of the electrodes for stimulation, as discussed above.

After recall of the rules of block 850, a determination of whether to initiate stimulation in block 854 may be made. The determination of initiation of therapy may be based upon various sensors provided with the subject 62 (e.g. sensor 61, 61'), initiation by the CTM 70, proximity to the CTM 70, or other appropriate initiation feature. The determination of whether initiation of the stimulation should begin in block 854 may be based upon the rules recalled in block 850.

If an initiation is not performed in block 854, a NO path 856 may be followed which may loop back to the initiation of stimulation at determination block 854. The loop may include a selected time delay, pause for receiving instructions from the CTM 70, or other appropriate further input.

If initiation stimulation is determined to occur, a YES path 860 may be followed to stimulate the subject per at least one of the recalled testing scheme schedules in block 864. As discussed above, a plurality of wave patterns may be determined and stored in block 844. The selected wave pattern or one of the selected wave patterns may be then used to stimulate the subject in block 864 once stimulation is initiated by following the YES path 860.

During the stimulation in block 864, a sensing and/or recording of the effectiveness and/or sensors relative to the subject 62 during the therapy may be made. For example oxygenation levels, breathe rates, EMG value, apnea-hypoapnea index (AHI) index or values may all or selectively be measured and/or recorded and stored for later analysis. For example, various sensors in the subject, such as the sensors 61, 61', may be used to sense various data relative to the subject 62. The information may be recorded and stored in selected memory modules, such as the memory module 54 on the ID 30 and/or may be transmitted for storing on additional memory modules such as the memory module 102 of the CTM 70.

Thus, the values from the sensors may be sensed and recorded in block 868. The data may be outputted in block 872 for further analysis, such as determining an effectiveness of the selected test stimulation pattern. The data may be outputted in one or more of the screens, such as the screen 92 of the CTM 70, the screen 124 of the CTM 74, or other appropriate output. The output may occur at any appropriate time, such as after a selected one of the sleep cycles, one of the completion of the scheduled waveform patterns, or other appropriate time.

After one or more test periods, a determination of whether more candidate waveforms are to be tested may be made in block 880. If a determination is made that additional waveforms should be tested, a YES path 884 may be followed to return to the initiation of stimulation determination block 854. Thus, the stimulation of the subject of 864 may be according to a different or selected additional waveform pattern to allow for sensing and recording of the subject 62 in block 868.

Once a selected number of waveforms have been tested, or no additional waveforms are determined to be tested block 880, a NO path 890 may be followed. When following the NO path 890 a determination of a select candidate waveform for stimulation may be made in block 894. The selected stimulation waveform in block 894 may be an optimal waveform for stimulation of the subject 62. An optimal waveform may be a waveform that provides a selected therapy to the subject, such as based upon the sensed data in block 868. Furthermore, it is understood, that a selected one of the sense values may be weighted greater than others and therefore an optimal waveform may not be based upon a single value and/or may include a selected optimal range for one sensed value, but not for another. A determination of an optimal waveform may include analysis of the sensor data, as discussed above, regarding the configuration of the electrodes for stimulation. The selection in block 894 may be based upon an efficacy of the therapy for the subject 62. The efficacy may be based on achieving selected or threshold sensor values. Threshold levels may be subject selected or determined, but may include low SPO2 values (e.g. less than about 90%), high breathing rates (e.g. above about 15 breathes per minute) or high heart rate (e.g. above about 100 BPM). In various embodiments, Quality of Sleep may be a therapy feedback loop for optimization. Thus, Quality of Sleep may be an indication of therapy effectiveness and/or efficacy.

The selected or optimal waveform in block 894 may be made or based on a determination of an efficacy of the treatment including the stimulation therapy based on the output results from block 868. The determination of the optimal waveform made in block 894 may be made based on the efficacy. The efficacy may be based on or determined as a comparison of the data values in block 868 to a predetermined value threshold and/or a subject threshold or response. For example, a threshold may be determined for oxygenation. The stored value in block 868 and output in block 872 may be compared to a predetermined oxygenation threshold. An efficacy (e.g. efficacy value) may be determined based on whether the predetermined threshold is achieved or exceeded and by what amount. Thus, a more or greater efficacious therapy may include a waveform that achieves a greater oxygenation than another waveform. It is understood, however, that efficacy may be based upon more than one value (e.g. sensor value) and/or weights of different parameters, such as those noted above.

After determining the selected waveform of block 894, the waveform may be set in block 900. By setting the waveform in block 900, the selected waveform may be programmed or selected in the ID 30 to provide stimulation to the subject 62 for a selected period of time. For example, the testing phase 820 may be used to test or select a waveform for stimulation of the subject 62 with the ID 30. After a selected testing phase, or selected time, the selected waveform may be selected in the ID 30 and set as the stimulation waveform. Thus, for example, after a period of testing (e.g. one month) the ID 30 may be set to a selected waveform for providing the selected (e.g. optimal) therapy to the subject 62.

The waveform may be set in block 910 at any selected time. For example, as noted above, the process 820 may be selected to run for a set period of time. It is understood, however, that the determination in block 894 may be substantially real time. For example, the processor 50 may receive inputs and determine a selected threshold is not met (e.g. oxygenation). If a threshold is not met, the processor may recall a different waveform from block 838 for stimulation. Thus, the process 820 may allow for substantially real time (e.g. once or more during a current or single sleep cycle) determination and stimulation with a waveform.

It is understood, however, that after a selected period of time, a new test phase may be selected or determined in block 910. Selecting new test phase in block 910 may be any appropriate selection of a new test phase, such as after a passage of a selected time, selection by a clinician such as transmitting a signal from the CTM 74, or other appropriate selection. Accordingly, the new test phase may be made in block 910.

If a new test phase is determined in block 910, a YES path 914 may be followed to construct or recall a list of possible candidate waveforms in block 834. The process 820, therefore, may be repeated at a selected time. It is understood that the list in block 834 may be the same list as discussed above, and simply be retested as the subject 62 may change over time (e.g. gain muscle rigidity, strength, or the like).

Further, if a new test phase is not determined to occur, a NO path 920 may be followed and the process 820 may end in block 924. Ending the process in 924 may include stimulating the subject 62 according to the selected waveform in block 900 for stimulating the subject in an appropriate time or manner. Thus, the process 820 may be used to test and/or select an appropriate or optimal waveform for the subject 62.

Accordingly, as discussed above, the ID 30 may be used to provide stimulation to the subject 62 in an appropriate manner. The ID 30 may be used to configure the electrodes or to provide stimulation to a selected configuration of the electrodes so the electrode tips 40, 44 in various patterns or configurations. Further, various waveforms may be used to stimulate the subject 62. These selected configurations and/or waveforms may be tested or selected over a selected period of time, such as after implantation of the ID 30. It is understood that a combination of both configurations of the electrodes, waveforms, or sensed information from the subject 62 may all be tested simultaneously, sequentially, or the like to determine an optimal configuration, waveform, and other factors or parameters relative to subject 62 to provide therapy to the subject 62. Thus, the ID 30 may be used to provide stimulation to the subject 62 in a manner to substantially reduce and/or eliminate fatigue of the lingual muscle 170 and/or provide a selected or optimal therapy to the subject 62 to provide therapy for selected conditions, such as OSA, UARS, or other appropriate conditions.

Figure 10:
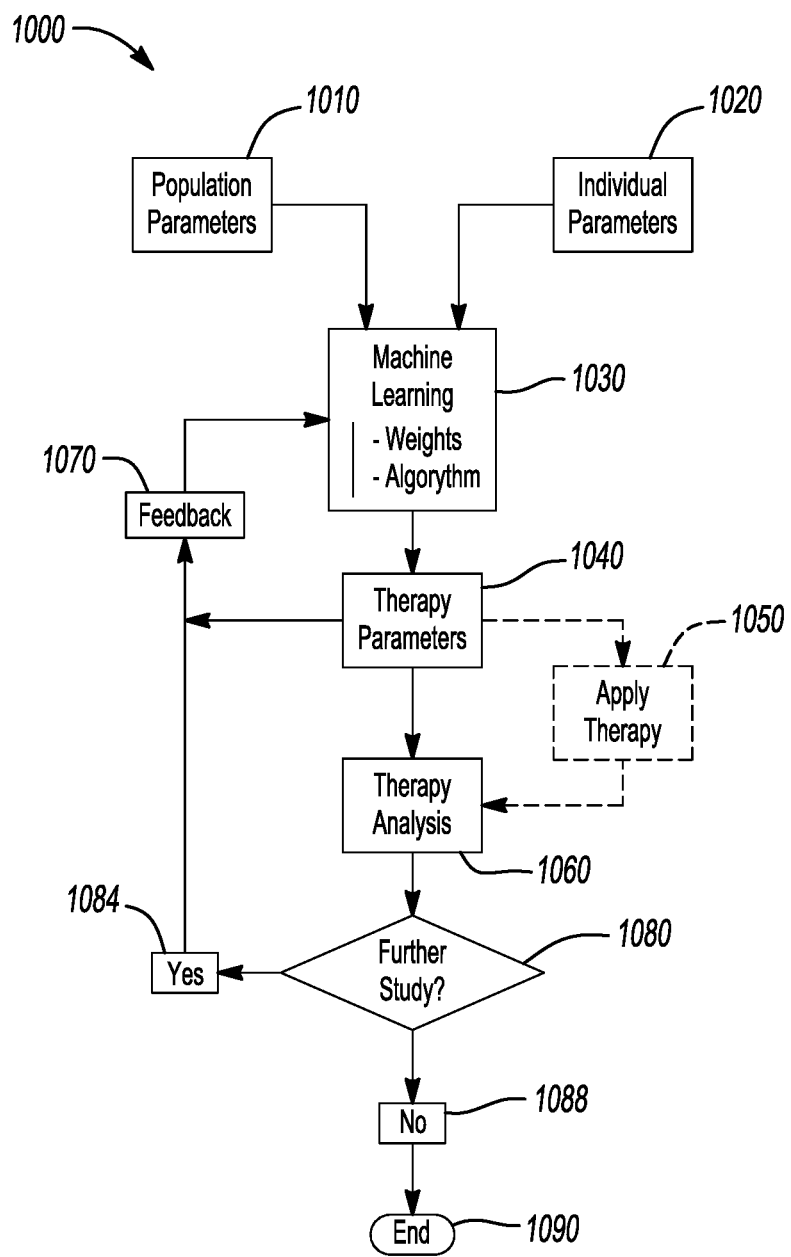
FIG. 10 is a flowchart illustrating a stimulation system use/training/testing, according to various embodiments.

Turning to FIG. 10, a process or system 1000 is illustrated. The system 1000 may be used to assist in generation of parameters for a therapy to the subject 62, or any appropriate subject. In various embodiments, the process 1000 may be a machine learning process that may incorporate or use any appropriate machine learning algorithm (e.g. regression analysis, supervised or unsupervised algorithms, neural networks, or combinations thereof). The machine learning process 1000 may allow for acquisition or usage of data from a plurality of subjects and/or one subject, for generation of a particular therapy parameter.

For example, population parameters or data 1010 may be collected. Individual parameters or data may also be collected in block 1020. The parameters may be substantially identical between the population in block 1010 and the individual in block 1020. For example, parameters may include body mass index (i.e. including body mass), blood pressure, oxygen saturation in blood and tissue, EMG (e.g. chin EMG, thoracic or arterial EMG, or the like), breathing rate, pulse rate, or other appropriate parameters. Parameter values may be collected from a population in block 1010 or from an individual in block 1020 and may include those collected during selected studies such as a sleep study. As discussed above, a sleep study of an individual or population of individuals may include acquisition of data in a polysomnography. In the sleep study, various parameters may be collected regarding the individual during an alert state, a sleep state, a vertical position, horizontal position, or other orientations of the subject. Various parameters may include those as discussed above, including oxygenation levels, brain waves, muscle activation in various areas of the body of a subject, and other appropriate parameters. The various parameters may be used to identify or determine onset and/or currents of an apneic episode. For example, a breathing rate, oxygenation level, or the like may be used to determine or understand a severity, length, or the like of an apneic episode. The subject, such as the subject 62, may then be stimulated or have therapy applied thereto in an appropriate manner to assist in correcting or stopping the apneic episode.

The population parameters or data 1010 may include data regarding a population, such as a plurality of patients. The data may include data regarding the patient (e.g. body mass and health conditions) and various parameters for stimulation of a lingual muscle for each of the population. Thus, the population data 1010 may include a stimulation parameters (e.g. waveform and/or lead configuration) for treatment of OSA. The population data may further include a determined efficacy (e.g. expert or clinician determined efficacy) for the applied therapy. The population data may include various inputs (e.g. sensor inputs and subject inputs) regarding the subject during stimulation. The inputs may include those as discussed above include apneic event duration, frequency, oxygen saturation, etc. Thus, the efficacy may be determined based on the various inputs during the stimulation.

Regardless, the population parameters from block 1010 and the individual parameters from block 1020 may be acquired and input into a machine learning system in block 1030. The machine learning system 1030 may include a selected algorithm, such as those discussed above and various weights for the parameters. The machine learning system may acquire and analyze the parameters from the population in block 1010 and individuals in block 1020. The weights and algorithm associated with the machine learning system in block 1030 may be used to determine an appropriate therapy parameter.

The therapy parameter may then be determined and output in block 1040. The therapy parameter may include various features, such as those discussed above, including stimulation waveforms, lead configurations, various inputs from sensors associated with a subject 62, and the like. As discussed above, various inputs may include accelerometers to indicate position of the subject 62, oxygenation sensors to determine an oxygen saturation in various locations of the subject, and other appropriate sensors including those discussed above.

The therapy parameters output in block 1040 may include parameters regarding an initiation of therapy, a waveform of therapy, a configuration of the electrodes for therapy, or the like. Further, therapy parameters may include a plurality of sets of therapy parameters that may be studied or tested relative to the subject 62, as discussed above. In various embodiments, however, the therapy parameters output in block 1040 may include a single set of parameters including a waveform, electrode configuration, and selected sensor inputs (e.g. for initiation of stimulation include subject position, breathe rate, etc.).

Thus, the ID 30 may be programmed after implantation based upon the machine learning system 1030 that may include population parameters from block 1010 and individual parameters from block 1020. In various embodiments, the individual parameters in block 1020 may include a sleep study of the individual subject, which may include information regarding apneic episodes during the sleep study. Accordingly, the therapy parameters in block 1040 may include initiating therapy based upon a determined position of the subject (i.e. with a sensor), signal received by the ID 30 regarding initiation of therapy, or the like. The therapy parameters from block 1040 may further include the specific waveform that may be selected (e.g. by a clinician), the population parameters 1010, or feedback, as discussed further herein.

The therapy parameters output in block 1040 may be used or applied to a subject, such as in optional application of therapy in block 1050. The application of therapy in block 1050 may include the application of therapy to the subject 62 based upon the therapy parameters output in block 1040. The therapy parameters may be stored in the ID 30 such as during an ID 30 programming, programming with the CTM's 70, 74, or other appropriate programming. The subject 62 may then have the therapy applied for a selected period of time in block 1050, such as over a certain number of sleep hours, sleep cycles, set period of time, or the like. It is understood that the application of therapy in block 1050, however, is not required for the process 1000, but is included or disclosed for clarity thereof.

A therapy analysis may happen in block 1060. The therapy analysis may include the data collected during the application of therapy in block 1050 based on the therapy output in block 1040. The therapy analysis in block 1060, however, may be an analysis of any appropriate therapy data. Therapy analysis may include data regarding a number of apneic episodes, length of apneic episodes, severity of apneic episodes (e.g. oxygen saturation, brain wave, or other appropriate considerations). The selection or analysis in block 1060 may be based upon an efficacy of the therapy for the subject 62 or population of subjects. The efficacy may be based on achieving selected or threshold sensor values and/or of subject or population feedback. Also, an increase or greater efficacy may be achieved when one or more thresholds is reached or values improved upon (e.g. greater oxygenation) relative to a different therapy parameter.

In various embodiments, efficacy may be determined or evaluated based on a reduction of a severity of apneic events. Various factors may include oxygen saturation levels, heart rate, and length of time of undesirable indications may relate to severity. For example, low or very low oxygen saturation levels (e.g. below about 85%) may be severe, where the lower the levels the more severe the apneic event. A very high heart rate (Indicating high sympathetic tone) (e.g. above about 100 BPM) may be sever, where the higher the levels the more severe the apneic event. Also, a long period (e.g. minutes) of undesirable factors (e.g. oxygenation levels, heart, rate, etc.) may be severe, where the longer the time period the more severe the apneic event. Also, the greater the number of apneic events may relate to a more severe or a less efficacious treatment. Other indications may include reduced or no airflow. In general, apnea event could be a trigger for other cardiac arrhythmias (slow HR<30 bpm, syncope pause more than 3 seconds, AF, etc.).

The therapy analysis may be performed by or with the ID 30, the CTM's 70, 74, or any appropriate system. The therapy analysis may include the determination of a success or optimization of a selected therapy output in block 1040. Accordingly, as discussed above, the therapy analysis in block 1060 may include a determination of the number of apneic episodes during a period of sleep (e.g. a rate of apneic episodes per sleep minutes or hours), and/or other factors of the subject 62.

The therapy analysis may be used to provide a feedback 1070 to the machine learning 1030. The feedback may include a simple feedback, such as a number of apneic episodes the selected therapy from block 1040, or other appropriate feedback. For example, the feedback may include the subject feedback regarding sleep success, sleep quality, or the like. The feedback, therefore, may be provided to the machine learning system 1030 to analyze or include the therapy analysis from block 1060 and the various population in individual parameters 1010, 1020.

As discussed above, machine learning may include selected algorithms and various features of the algorithms, such as weight, to assist in determining an appropriate therapy parameter. Thus the feedback 1070 may allow for a change or optimization of therapy parameters that may then be output in block 1040. The therapy analysis may then occur in block 1060.

The process 1000 may then loop, therefore, to analyze a plurality of therapy analysis from block 1060, and/or parameters to provide or determine a therapy for the subject 62.

The process 1000, therefore, can be understood to be a loop or iterative process to achieve a therapy for the subject 62. The loop process 1000, therefore, may include an end-loop determination, such as determining whether further study is to occur in block 1080. If further study is to occur in block 1080, a YES path 1084 may be followed into the feedback loop 1070. Thus, the machine learning process 1000 may be used to determine an optimal therapy for the subject 62, or selected therapy for the subject 62, based upon the various therapy analyses in block 1060. The feedback 1070 may be long term, such as over a plurality of sleep cycles, and/or may be short term or real time, such as during a current sleep cycle. In real time, for example, the feedback may be that an apneic event is extending longer than a selected time threshold or that oxygenation levels are below a threshold. Thus, the therapy parameters may be altered in real time once the determination is made that one or more thresholds have been reached If further study is not required or selected, a NO path 1088 may be followed to end in block 1090. The ending in block 1090 may be a programming of the ID 30 for a selected time, such as a selected period of time, selected sleep cycle, or the like. The therapy for the subject 62 may be based upon the analysis, therefore, of the subject 62 individually and/or a population of subjects. The population of subjects from which the population parameters are required in block 1010 may include those with or that have been diagnosed with sleep apnea, those that have not been diagnosed with sleep apnea, individuals of various backgrounds, and the like. Thus, the population parameters 1010 may be used to provide or determine a selected or universal set of parameters regarding a subject, including those with sleep apnea. The process 1000, therefore, may be used to provide a therapy to the subject without limitation to only an individual parameter, such as an individual sleep study of the individual 62 to have therapy applied thereto.

Thus, as discussed above, a therapy may be applied to the individual or subject 62 the ID 30 based upon various parameters. The parameters may include waveform of stimulation, configuration of electrode contacts for stimulation, sensor inputs to determine when and/or a magnitude of stimulation, and/or other parameters for therapy and input. Further, various portions of the stimulation system 20, such as the processor 50 of the ID 30, may execute instructions per selected processors for determination of whether stimulation should be initiated, as discussed above in the process 480. Also, the system 20 may be used to selected and/or implement one or more stimulation parameters (e.g. waveform, electrode configuration, etc.) for providing a therapy to the subject with a selected efficacy. The system 20 may operate to make the determination and/or implement the therapy by one or more of the processes 620, 820, or 1000 as discussed above. Also, a combination of one or more may be used, such as selecting both a waveform and an electrode configuration for therapy.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium (e.g. memory module) and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors (e.g. processor module), such as one or more digital signal processors (DSPs), general purpose microprocessors, graphic processing units (GPUs), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for activating a lingual muscle of a subject, comprising:
   comparing a set of data regarding the subject to sets of data regarding a population, wherein the set of data regarding the subject includes a set of individual parameters regarding the subject and sets of data regarding the population includes sets of population parameters regarding the population;
   identifying a set of population parameters from the sets of population parameters based on the comparison;

recalling a first set of parameters for activating the lingual muscle based on the identified set of population parameters;
delivering a stimulation to the subject based on the first set of parameters;
receiving a signal regarding the subject in response to delivery of the stimulation; and
evaluating a first efficacy of the stimulation based on the received signal and a machine learning algorithm.

2. The method of claim 1, further comprising:
receiving the set of data regarding the subject.

3. The method of claim 1, wherein the machine learning algorithm includes evaluating a sleep characteristic of the subject.

4. The method of claim 3, wherein evaluating the sleep characteristic of the subject includes evaluating at least one of a number of apneic episodes, a frequency of apneic episodes, a breath rate, an oxygen saturation level, or combinations thereof.

5. The method of claim 4, wherein the signal is transmitted with the sleep characteristic of the subject.

6. The method of claim 5, further comprising:
operating a processor system to execute the machine learning algorithm;
wherein the machine learning algorithm is configured to evaluate the signal including the sleep characteristic based at least on a weight of each sleep characteristic.

7. The method of claim 6, wherein recalling the first set of parameters comprises recalling the first set of parameters at a first time, the method further comprising:
altering the first set of parameters based on the evaluation of the sleep characteristic; and
generating an altered set of parameters operable to be recalled at a second time.

8. The method of claim 7, further comprising:
comparing the altered set of parameters and the set of data regarding the subject; and
selecting at least one parameter from the altered set of parameters based on the comparison of the altered set of parameters and the set of data regarding the subject.

9. The method of claim 4, wherein the first efficacy is determined based on determining the relative value of the sleep characteristic of the subject to a threshold value of a selected sleep characteristic.

10. The method of claim 1, further comprising:
operating a processor system to execute the machine learning algorithm;
transmitting an efficacy signal with the first efficacy to the processor system; and
selecting at least one parameter from the recalled first set of parameters based on the transmitted efficacy signal.

11. The method of claim 6, wherein delivering the stimulation comprises delivering the stimulation at a first time, the method further comprising:
determining that the first efficacy is outside of the threshold;
selecting a parameter from the first recalled set of parameters based on the determination that the first efficacy is outside of the threshold; and
transmitting the parameter for stimulation of the subject at a second time.

12. The method of claim 11, wherein evaluating the first efficacy comprises determining a value of at least one of a number of apneic episodes, a frequency of apneic episodes, a breath rate, an oxygen saturation level, or combinations thereof relative to a threshold.

13. A method for selecting a parameter for activating a lingual muscle of a subject, comprising:
comparing a set of data regarding the subject to sets of data regarding a population, wherein the set of data regarding the subject includes a set of individual parameters regarding the subject and sets of data regarding the population includes sets of population parameters regarding the population;
identifying a set of population parameters from the sets of population parameters based on the comparison;
recalling a first set of parameters for activating the lingual muscle based on the identified set of population parameters;
selecting a first parameter from the recalled first set of parameters;
operating a processor system to:
receive a signal regarding a subject therapy parameter of the subject during a stimulation of the subject at a first time with the selected first parameter; and
determine a first efficacy of the stimulation at the first time by evaluating the subject therapy parameter with a machine learning algorithm regarding a first efficacy of therapy for the subject;
compare the first efficacy to a threshold efficacy;
output a comparison value based on the compared first efficacy to the threshold efficacy.

14. The method of claim 13, further comprising:
generating an altered set of parameters to be recalled at a second time based on the output comparison.

15. The method of claim 14, further comprising:
recalling at the second time the altered set of parameters;
selecting a second parameter from the recalled altered set of parameters based on a comparison of the identified set of population parameters and the set of individual parameters regarding the subject;
operating the processor system to:
receive a second signal regarding the subject therapy parameter of the subject during a stimulation of the subject at the second time with the selected second parameter; and
determine a second efficacy of the stimulation at the second time by evaluating the subject therapy parameter with the machine learning algorithm;
compare the second efficacy to the threshold efficacy;
output a second comparison value based on the compared second efficacy to the threshold efficacy.

16. The method of claim 13, wherein the first set of parameters includes a stimulation waveform, an electrode configuration, or combinations thereof.

17. The method of claim 14,
wherein the altered set of parameters includes at least one of an altered stimulation waveform, an altered electrode configuration, or combinations thereof.

18. A system for activating a lingual muscle of a subject, comprising:
a memory system to store a set of data regarding the subject and sets of data regarding a population, wherein the set of data regarding the subject includes a set of individual parameters regarding the subject and sets of data regarding the population includes sets of population parameters regarding the population; and
a processor system configured to execute instructions to:
compare the set of individual parameters regarding the subject to the sets of population parameters regarding the population;
identify a set of population parameters from the sets of population parameters based on the comparision;

recall a first set of parameters for activating the lingual muscle based on the identified set of population parameters;

deliver a stimulation to the subject based on the first set of parameters;

receive a signal regarding the subject in response to the delivery of the stimulation; and evaluate a first efficacy of the stimulation based on the received signal and a machine learning algorithm.

19. The system of claim 18, further comprising:
a stimulation system having a power source, a first lead end, and a second lead end; and
wherein the stimulation system is configured to stimulate the subject through the first lead end and the second lead end.

20. The system of claim 19, further comprising:
a sensor configured to sense the set of individual parameters and transmit a signal to the processor system including a sensed value of the set of individual parameters.

21. The system of claim 20, wherein the processor system is configured to compare the first efficacy to a threshold efficacy, and wherein the processor system is further configured to execute instructions to generate an altered set of parameters to be recalled at a second time based on the comparison.

22. The system of claim 18, wherein the first set of parameters includes a stimulation waveform, an electrode configuration, or combinations thereof.

\* \* \* \* \*